United States Patent
Koganov

(10) Patent No.: US 11,766,397 B2
(45) Date of Patent: *Sep. 26, 2023

(54) **BIOACTIVE COMPOSITIONS COMPRISING *FICUS* SERUM FRACTON AND METHODS TO REDUCE THE APPEARANCE OF SKIN HYPERPIGMENTATION**

(71) Applicant: ISP INVESTMENTS LLC, Wilmington, DE (US)

(72) Inventor: Michael Koganov, White Plains, NY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 415 days.

This patent is subject to a terminal disclaimer.

(21) Appl. No.: 16/706,677

(22) Filed: Dec. 7, 2019

(65) Prior Publication Data

US 2020/0383897 A1 Dec. 10, 2020

Related U.S. Application Data

(63) Continuation-in-part of application No. 13/821,775, filed as application No. PCT/US2011/051066 on Sep. 9, 2011, now abandoned.

(60) Provisional application No. 61/381,442, filed on Sep. 10, 2010.

(51) Int. Cl.
*A61K 8/9789* (2017.01)
*A61Q 19/02* (2006.01)

(52) U.S. Cl.
CPC ............ *A61K 8/9789* (2017.08); *A61Q 19/02* (2013.01)

(58) Field of Classification Search
None
See application file for complete search history.

(56) References Cited

PUBLICATIONS

Hagerman et al., Protein Precipitation Method for the Quantitiative Determination of Tannins, 1978, J Agric Food Chem, 26: 809-812.*

* cited by examiner

*Primary Examiner* — Terry A McKelvey
*Assistant Examiner* — Catheryne Chen
(74) *Attorney, Agent, or Firm* — William J. Davis; Nathalie Tietcheu

(57) ABSTRACT

The present invention provides bioactive compositions comprising *Ficus* serum fraction derived from *Ficus* cell juice of fresh *Ficus* leaves and a process of preparing the *Ficus* serum fraction. The compositions have biological activity capable of reducing skin hyperpigmentation.

11 Claims, 11 Drawing Sheets

BIOACTIVE COMPOSITIONS COMPRISING *FICUS* SERUM FRACTON AND METHODS TO REDUCE THE APPEARANCE OF SKIN HYPERPIGMENTATION

CROSS REFERENCE TO RELATED APPLICATIONS

This application is a continuation of U.S. patent application Ser. No. 13/821,375, filed Jun. 3, 2013, which is a U.S. National Phase filing under 35 U.S.C. § 371 of International Application No. PCT/US11/51066, filed Sep. 9, 2011, and published as WO 2012/034060-A2 on Mar. 15, 2012, which claims benefit of priority from U.S. Provisional Patent Application Ser. No. 61/381,442, filed Sep. 10, 2010. The entire contents of each of the prior applications are incorporated herein by reference in their entirety.

FIELD OF THE INVENTION

The present invention relates to the field of skin lightening by topical application of cosmetic compositions to the skin. The invention further relates to topical skin lightening compositions comprising *ficus* serum fraction. The invention also relates to methods for reducing the appearance of skin hyperpigmentation by topically applying the cosmetic composition to hyperpigmented areas in order to disrupt one or more steps in melanin synthesis.

BACKGROUND OF THE INVENTION

Human skin comprises three principal layers: the epidermis, the dermis, and the subcutaneous fat layer. The epidermis comprises four layers (from top to bottom): the stratum corneum, the granular layer, the spiny layer, and the basal layer. A separate fifth layer, the stratum lucidum, may be present between the stratum corneum and granular layer. The basal layer produces cells which gradually migrate upward to form the other epidermal layers. As these cells migrate upward, they lose their central nucleus and start to produce skin proteins (keratins) and fats (lipids). These cells are identified as keratinocytes when present in the upper layers of the epidermis. Melanocytes are another class of cells located in the basal layer of the epidermis. Melanocytes are responsible for the production of melanin, which is a primary factor in skin pigmentation.

Melanin is produced by a complex set of reactions within the melanocyte involving, at a basic level, the enzyme tyrosinase and L-tyrosine as a substrate. Tyrosinase catalyzes the conversion of L-tyrosine to DOPA (L-3,4-dihydroxyphenylalanine) and of DOPA to dopaquinone. Dopaquinone undergoes further conversion to form melanin. Melanin aggregates in organelles known as the melanosomes which are transferred to keratinocytes along slender filaments of the melanocyte known as dendrites. There are approximately 1500 gene products expressed in melanosomes with 600 of them being expressed at any, given time, and 100 of them believed to be unique to the melanosome. In addition, there are many regulatory elements involved in signaling, in the transport of melanosomes within the melanocyte, and in the transfer of melanosomes to the keratinocytes.

The production of melanin can be triggered by a variety of external and internal events. For example, melanocytes produce additional melanin when skin is subjected to UV radiation. The melanin is then transported via melanosomes to the keratinocytes, which then leaves the skin with a "tanned" appearance. Once the UV light is removed the melanocytes return to normal levels of melanin production. Inflammation may initiate hyperpigmentation by direct stimulation of the melanocytes by mediators such as IL-1, endothelin-1, and/or stem cell factor. Reactive oxygen species, such as superoxide and nitric oxide, generated in damaged skin or released as by-products from inflammatory cells may be stimulators of melanocytes.

Over time, chronic UV exposure and other intrinsic and extrinsic aging factors may lead to permanent gene expression changes in keratinocytes and/or melanocytes resulting in age-related hyperpigmented spots. The mRNA levels of some melanogenesis associated genes (for example, tyrosinase, TYRP1) are reported to increase actinic lentigos (age spots). There may also be accentuation of the epidermal endothelin cascade and a role for stem cell factor in hyperpigmentation. These changes can result in overproduction of melanin and resultant hyperpigmented spots that persist even when an insult, such as UV exposure, is avoided. Even beyond hyperpigmented spots, chronic. UV exposure and other intrinsic and extrinsic aging factors may lead to more subtle changes in skin tone. Often these changes are described as uneven tone or as a mottled appearance. At least one study suggests that age spots can sometimes add 10 to 12 years of perceived age to a person and that melanin distribution can drive tone dependent age perception. Thus, there is a desire to provide compositions and methods of treatment that can improve the appearance of hyperpigmented skin, such as age spots.

Over recent years, consumers have increasingly demanded "natural" cosmetic products. As a result, cosmetic manufacturers have incorporated more plant-based materials into their cosmetic formulations. Although various plants have been used for hundreds or even thousands of years for a variety of reputed indications, until recent times it has not been possible to clinically verify purported effectiveness or to identify new potential uses based upon the underlying science of the plant's bioactivity. With recent advances in science, researchers are now better able to assess the efficacy and/or potential new uses for plants that until recently were only supported by folklore. Because of the newness of the science, and because the number of plants that could potentially be utilized as cosmetic bioactives is so immense, the vast majority of plants have not yet been fully investigated.

Many of the methods used for extracting botanical components from plants involve techniques that are harmful to the plant tissue composition and/or the bioactive components of interest contained in that tissue. Consequently, traditional extraction methods often fail to deliver the full spectrum of activities that exist within the plant cells and thus the full potential of botanical-based cosmetic formulations is not realized. In addition, many traditional extraction methods utilize harsh chemical solvents, which are not "natural" and thus are materials that consumers want to avoid applying to their skin. Furthermore, these solvent-based processes produce toxic chemical wastes that can harm the environment if not properly handled and disposed of as hazardous waste.

Just because a material is "natural" does not guarantee that it is free from undesired substances that would make the material suitable for use on skin, however. For example, many plants contain photosensitizers such as pheophorbides and/or contact allergens such as proteins. At levels naturally found in many common plants, pheophorbides and/or proteins do not cause concern for most people. However, when plant materials are condensed to a highly concentrated form, such as through extraction, these materials can be present at levels that cause skin irritation and allergic reactions, including rashes. Even when these materials are present at their natural levels, however, there are still many sensitive individuals who experience negative skin reactions.

Furthermore, as demands for natural products have increased, so have concerns about protecting earth's natural resources. Many of the "natural" ingredients that consumers desire are derived from bioresources that are depleted and/or destroyed when harvested for use in consumer products. Thus, consumers' desire for natural, more earth-friendly products can ironically lead to the destruction of the very bioresources they aim to preserve Thus, there is a need for natural bioactive botanical compositions that maintain their spectrum of desired bioactivity, are suitable for topical skin application, and are not prepared using harsh chemical solvents. Furthermore, there is a need for cosmetic compositions containing such bioactives that are effective for reducing areas of skin hyperpigmentation. In addition, there is a need for such bioactive materials that can be harvested and processed in an ecologically sound, sustainable manner.

These and other objects of the present invention will become apparent in light of the following disclosure.

SUMMARY OF THE INVENTION

The present invention provides *Ficus* serum fraction derived from fresh *Ficus* leaf cell juice. The present invention also provides cosmetic compositions comprising *Ficus* serum fraction. The *Ficus* serum fraction is present in the composition at an amount effective for attaining the desired skin lightening result.

The invention also relates to methods for reducing the appearance of skin hyperpigmentation by topically applying the cosmetic composition to hyperpigmented areas in order to disrupt one or more steps in melanogenesis.

BRIEF DESCRIPTION OF THE DRAWINGS

It is believed that the present invention will be better understood from the following description taken in conjunction with the accompanying drawings. The referenced drawings are not to be construed as limiting the scope of present invention.

DETAILED DESCRIPTION OF THE INVENTION

Figure 1:
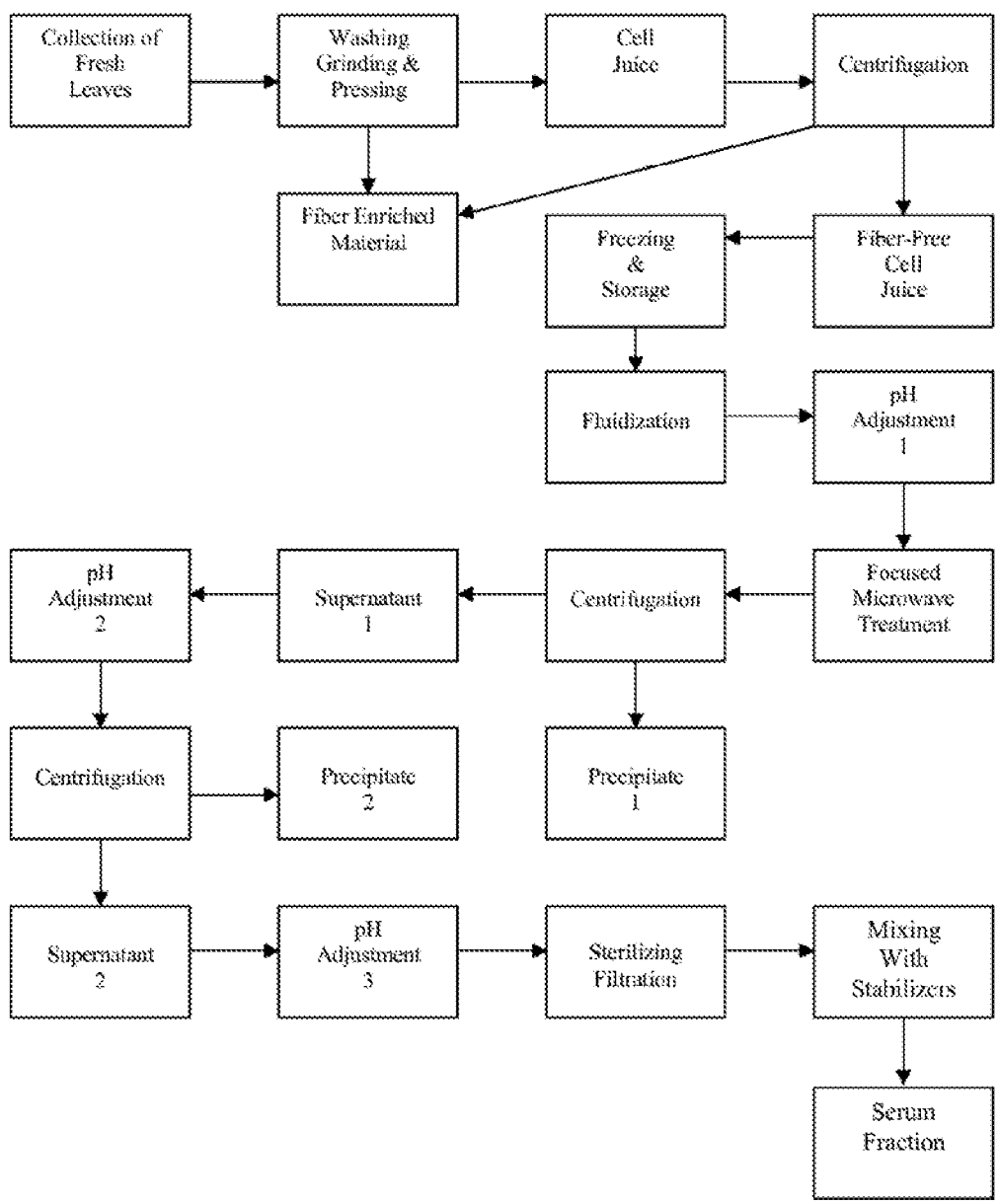
FIG. 1 is a schematic drawing of the process for preparing the bioactive serum fraction from fresh *ficus* leaves.

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a human skin surface such as the epidermis.

The term "dermatologically acceptable" as used herein means that the compositions or components described are suitable for use in contact with human skin tissue without undue toxicity, incompatibility, instability, allergic response, and the like.

The term "safe and effective amount" as used herein means an amount of a compound or composition sufficient to significantly induce a positive benefit.

The term "post-inflammatory hyperpigmentation" as used herein refers to an acute to chronic increase in pigmentation as a response to a transient inflammatory event. Post-inflammatory hyperpigmentation is particularly prevalent in, but not limited to, dark skin subjects. Post-inflammatory hyperpigmentation typically subsides once the transient inflammatory event dissipates. Examples of transient inflammatory events include, but are short-term UV exposure.

The term "hyperpigmented spot" as used herein refers to a defined area of skin wherein the pigmentation is greater than that of an adjacent area of skin due to localized and chronic or systemic overproduction of melanin. Hyperpigmented spots typically are between about 2 mm and about 10 mm in diameter but smaller or larger spots are possible. Hyperpigmented spots can include one or more of age spots, sun spots, solar lentigos, hypo-melanotic lesions, freckles, and melasma spots.

The term "age spots" as used herein refers to a hyperpigmented spot wherein the pigmentation is due to localized and chronic overproduction of melanin caused by intrinsic or extrinsic aging factors.

The term "skin tone agent" as used herein refers to an agent that regulates melanin production signals, synthesis of melanin, systemic transfer of melanin between the melanocyte and the keratinocyte, and/or melanin degradation. Skin tone agents can improve the appearance of uneven skin tone by acting as a lightening or pigmentation reduction cosmetic agent.

The term "skin tone" as used herein refers to the overall appearance of melanin in the skin caused by the systemic, rather than transient, synthesis of melanin. Skin tone is typically characterized over a larger area of the skin. The area ideally may be than 100 mm2, but larger areas are envisioned such as the entirety of the facial skin or any of the facial skin surfaces. Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data. Suitable chromophore mapping techniques are discussed in the example below.

The term "facial skin surface" as used herein refers to one or more of forehead, periorbital, cheek, perioral, chin, and nose skin surfaces.

The term "traditional extract" as used herein refers to those extracts produced by solvent extraction of compounds from plant material; the plant material can be dehydrated (i.e., dried) and/or undehydrated (e.g., fresh or only partially dehydrated) plant material.

I. Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

The compositions of the present invention are useful for reducing the appearance of skin hyperpigmentation associated with melanin. As used herein, "reducing the visible appearance of skin hyperpigmentation" includes skin lightening. Skin lightening involves diminishing, minimizing and/or effacing existing melanin in skin (therapeutic), and/or delaying, minimizing and or preventing the formation of melanin in skin (prophylactic), including hyperpigmented regions of skin. As used herein "hyperpigmented region" means a localized region of high melanin content and includes age spots, liver spots, blotchiness, mottling, melasma, chloasma, freckles, post inflammatory hyperpigmentation or sun-induced pigmented blemishes.

A. *Ficus* Serum Fraction

*Ficus*, the fig genus, consists of numerous species and is found world-wide. The *Ficus* genus should not be confused with the *ficus* species, the prickly pear cactus 25 *Opuntia ficus-indica* (L.) Cactaceae (Barbera et al., PAST AND PRESENT ROLE OF THE INDIAN-FIG PRICKLY-PEAR (*OPUNTIA FICUS-INDICA* (L.) MILLER, CACTACEAE) IN THE AGRICULTURE OF SICILY. *Economic Botany* 46(1):10-20. 1992.) Notable species of the fig genus include *Ficus carica* (the common fig), *Ficus religiosa* (the Bo tree which sheltered the Buddha as he divined the "Truths"), *Ficus elastica* Roxb. exHorneum. (the rubber tree), *Ficus behghalensis* (the banyan tree) and *Ficus racemosa* (syn. glomerata, the giant cluster tree).

Within the general category of fruits, figs are examples of syconia, multiple fruits with a distinctive "inside-out" structure. These comprise collections of droplets, which are fleshy hollow receptacles, each with a small opening at the apex called an ostiole. Tiny flowers are massed on the inside walls and are not visible externally.

As one of the oldest known human foods, *Ficus* spp. (figs) have a long-standing safety profile. Fresh or dry fruits, tree bark, leaves, twigs, latex, and young branches of the fig have been used for various purposes throughout history. Some of these historical uses include treatment for sores, ulcers, cancerous growths, tumors, abscess, gout, chronic cough, lung problems, chronic diarrhea, constipation, rheumatism, gonorrhea, hemorrhoids, diabetes, vomiting, excema, leprosy, and warts.

The *Ficus* serum fraction (hereinafter "FSF") of the present invention is derived from the cell juice of fresh *Ficus* leaves. Cell juice mechanically separated from fresh leaves is fractionated using pH adjustments, focused microwave radiation, centrifugal separation, and sterilizing filtration to obtain pheophorbide free and protein free *Ficus* serum fraction. The resulting *Ficus* Serum Fraction consists essentially of the *Ficus* leaf cell cytoplasm. In particular embodiments, the *Ficus* cell juice is derived from the *Ficus* species selected from the group consisting of *F. benghalensis, F. carica, F. elastica, F. microcarpa, F. trigonata*, and combinations thereof.

Compositions of the present invention include a safe and effective amount of *Ficus* serum fraction. The composition may contain FSF in an amount from 0.01% to 50%, in one embodiment from 0.05% to 20%, in another embodiment from 0.2% to 10%, by weight of the composition. In yet another embodiment the composition comprises from 1% to 5%, and in yet another embodiment from 1% to 3% FSF by weight of the total composition.

The present investigators have found that *Ficus* serum fraction produces superior skin lightening effects in comparison to traditional *Ficus* extract, including lightening of hyperpigmented regions in mammalian skin, when applied topically to the skin. The subject invention is not to be limited by theory, but is believed to operate by the inhibition of processes involved in melanin production (melanogenesis), including preventing, reactive oxygen/oxygen radical stimulation (oxidative stress) of melanocytes which results in initiation of the melanin production pathway within the melanocytes (e.g., which can occur 30 with UV- or sunlight exposure).

Preparation of the *Ficus* Serum Fraction

Figure 11:
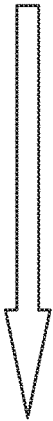
FIG. 11 summarizes the different types of compounds typically extracted using common solvents over a range of differing polarities (Table 1x)

The method used to separate compounds from plant matter, such as by extraction with a solvent, determines which compounds are isolated. Consistent with the general principle of "like dissolves like," the choice of extraction solvent largely determines the type and number of compounds that will result from any particular extraction technique. For instance, polar compounds are extracted out by using polar solvents, while non-polar compounds are extracted out by using non-polar solvents. This results in the isolation of only a narrow range of compounds from the total spectrum of compounds that may be present. FIG. 11, Table 1x summarizes the different types of compounds typically extracted using common solvents over a range of differing polarities.

The *Ficus* Serum Fraction of the current invention is not prepared by solvent extraction, but rather is prepared by separating the fresh cell juice found in the plant leaves from the rest of the plant matter. This cell juice, because it has not been subjected to an extraction process, contains the full spectrum of compounds found in fresh *ficus* leaves. In contrast, extracts contain only the narrow range of compounds that can be separated with a particular solvent. Thus, the resulting *Ficus* Serum Fraction contains a much broader range of potentially active compounds than does an extract.

Furthermore, many extracts are not prepared from fresh leaves, but rather from dried plant material, which has undergone degradation due to dehydration. During dehydration, the cell walls are compromised, causing the depredation of compounds through mechanisms such as hydrolysis, oxidation, polymerization, Maillard reactions, and isomerization. When the dried leaves are extracted, the resulting extract thus contains these degradation products that were not originally present in the fresh plant matter; further, the extract contains only that range of compounds that can be isolated by the particular solvent. Accordingly, the composition of the resulting dry leaf extract greatly differs horn that of *Ficus* Serum Fraction.

The method for making a *Ficus* Serum Fraction composition comprises the steps of: (a) separating *ficus* cell juice from clean, fresh, un-wilted *ficus* leaves to obtain fresh *ficus* cell juice, wherein no exogenous liquid is added prior or during said separating; (b) filtering said fresh *ficus* cell juice to obtain fiber-free cell juice; and (c) fractionating said fiber-free cell juice to obtain *Ficus* Serum Fraction. The fractionating step comprises the steps of: (1) removing chlorophyll from said fiber-free cell juice to obtain Supernatant I; (2) removing pigments and proteins from Supernatant I to form *Ficus* Serum Fraction; and (3) optionally adding stabilizer to said *Ficus* Serum Fraction.

In some embodiments, stabilizer is selected from the group consisting of antioxidants, chelating agents, preservatives, and mixtures thereof. In particular embodiments, stabilizer is selected from the group consisting of sodium metabisulfite, potassium sorbate, sodium benzoate, sodium methyl paraben, pentylene glycol, and mixtures thereof.

In particular embodiments, the step of removing chlorophyll from the fiber-free cell juice comprises: (i) adjusting the pH of said fiber-free cell juice to about 3 to obtain pH-adjusted fiber-free cell juice; (ii) heating said pH-adjusted fiber-free cell juice to about 90 C for about 1 minute; (iii) cooling said pH-adjusted fiber-free cell juice to about 30 C; and (iv) separating said pH-adjusted fiber-free cell juice into Precipitate and Supernatant I.

In particular embodiments, removing pigments and proteins from Supernatant I comprises: (i) adjusting the pH of Supernatant I to 7.5 to form pH-adjusted Supernatant I; (ii) separating pH-adjusted Supernatant I into Precipitate II and Supernatant II; (iii) adjusting the pH of Supernatant II to 3.6 to form pH adjusted Supernatant II; and (iv) separating pH-adjusted Supernatant II into Precipitate III and *Ficus* Serum Fraction.

Fresh *ficus* leaves are used to prepare the *Ficus* serum fraction. The preparation method herein maintains the integrity of the bioactive components inherently present in the *ficus* leaves, resulting in the *Ficus* serum fraction having superior activity. Care is taken to preserve the leaf integrity during harvesting and transport, so as to minimize environmental factors such as moisture loss and biological degradation. All steps are completed in the shortest possible period of time to minimize exposure of the fresh leaves to sun, high temperature, and other negative environmental factors.

In particular embodiments, the *Ficus* leaves are selected from the group of *Ficus* species consisting of *F. benghalensis, F. carica, F. elastica, F. microcarpa, F. trigonata*, and combinations thereof.

Harvesting, such as by hand or mechanical cutting, is conducted in a manner that avoids or minimizes the chopping, mashing, crushing, or other type of injury to the leaf. Harvest and transport should be conducted in a manner to avoid wilting due to moisture loss. In one embodiment, the fresh *ficus* leaves used to prepare *Ficus* serum fraction contain at least 90% of their original moisture content, in another embodiment at least 95%, and in another embodiment at least 98% of the original moisture content present at the time of harvesting.

Because up to 30% of a *Ficus* plant's leaves can be harvested at one time without adversely affecting the plant's viability, re-growth of leaves for future harvest can occur numerous times from the same plant. Thus, throughout its full, natural life span, the *Ficus* plant can continue to grow and be a part of the surrounding ecosystem while providing repeated leaf harvests for preparing bioactive cosmetic compositions. This harvest method is preferred, as it promotes sustainability of natural resources.

Although not as preferred, less sustainable collection methods can also be used, such as with large-scale mechanical harvesting that removes the bulk of the plant and does not leave a viable portion for re-growth. Even with this more aggressive harvest method, however, care is taken to minimize *Ficus* leaf injury that could lead to microbial growth, moisture loss, intensification of oxidation, polymerization, isomerization, and hydrolysis processes (i.e., unwanted catabolic processes) in collected leaves. For example, in one embodiment of the present invention, *Ficus* plants are cut and collected by hand as whole plants. In another embodiment, plant leaves are cut using harvesting equipment.

Delivery time of cut plant material to the processing facility and exposure of the leaves to sun, high temperature, and other negative environmental factors, should be minimized to prevent the impact of unwanted degradation processes as described above. For example, in one embodiment of the present invention, the delivery time for the plant for further processing does not exceed 30 minutes from the time of cutting. In another procedure involving immediately placing the *Ficus* leaves into Styrofoam coolers containing bags of frozen gel packs to help maintain freshness and natural moisture content during overnight delivery to the processing facility. Other post-cutting procedures that achieve the results described above may be used as well.

The *Ficus* leaves are then gently washed in order to remove the soil particles and other debris prior to processing. In one embodiment, the washing is achieved using a low-pressure rinse for a short duration under conditions to prevent the initiation of the release of the cell juice from the leaves, to cause injury, or to remove valuable components. For example, in one embodiment of the present invention, the washing of the Ficus leaves is accomplished in less than or equal to 5 minutes with a water pressure of less than or equal to 1 kg/cm2. Residual water wash should not contain any green or yellow pigments; absence of such pigments indicates the absence of subsequent injury. The excess water is then removed from the washed leaves in order to keep the dry matter content as close to natural level as possible.

The washed fresh ficus leaves are then mechanically separated to liberate the cell juice, which contains most of intracellular material of parenchyma cells, from the fiber enriched material, which predominately contains cell walls. Importantly, no exogenous solvent (e.g., water, hexane, acetone, ethanol) is added during the separation process. As used herein, "exogenous solvent" means any solvent that is not inherently present in the plant material, but is placed in contact with the plant material for the purpose of separating e.g., extracting) compounds from the plant material.

Liberating the cell juice from the washed leaves comprises grinding, maceration, and pressing to obtain the liquid intracellular content (i.e. the cell juice) and to separate it from fiber enriched material. In one embodiment, a hammer mill (Model VS 35, Vincent Corporation, Tampa, Fla.) having a 5 HP engine and a set of screens is used to grind the leaves to yield leaf tissue particles of suitably small size in a shortest amount of time and without significant increase of biomass temperature. In this embodiment, the hammer mill is set to produce the maximum size of macerated leaf particles of ≤2.0 centimeters during ≤10 seconds of treatment, where the temperature of macerated fresh leaves is increased by less than or equal to only ≤2° C. plant material.

Exposure of ground and macerated Ficus leaves is minimized to prevent the impact of unwanted catabolic processes, as described above. The Ficus leaves are processed in a short time and without significant increase in temperature. Immediately after grinding and maceration, the Ficus leaves are pressed to obtain cell juice from the macerated fresh leaves. In one embodiment, this is accomplished using a horizontal, continuous screw press (Compact Press "CP-6", Vincent Corporation, Tampa, Fla.), equipped with a cone supported by compressed air. The pressure on the cone in this embodiment is maintained at a level of greater than or equal to 15 kg/cm2, screw speed is at 12 rpm, and the cell juice temperature increase is less than or equal to 5° C.

This treatment yields fiber enriched material and cell juice. The residual small fiber particles are then removed from the cell juice, as they can absorb valuable cell juice components and also may block equipment hoses and pumps. For example, these particles can be removed by filtration or low; speed centrifugation. In one embodiment, these particles are removed by clarification using a continuous flow centrifuge (Model 12-413V, AML industries, Inc., Hatboro, Pa.) with full-automatic discharge unit. At a flow rate of 2 liter/min, retention time for cell juice clarification at ≤2,250 g is ≥100 seconds. This regimen produces fiber free cell juice. The precipitate containing small fiber particles is collected and combined with the rest of the fiber enriched material that was produced after pressing of the fresh leaves.

If desired at this point, the cell juice can be frozen in air-tight, non-reactive containers to preserve for later processing. In one embodiment, the cell juice is promptly placed in tightly closed 15 liter rectangular HDPE containers and frozen at −30° C. Solid state frozen cell juice is kept at this low temperature for further utilization.

The frozen cell juice can then be transformed back into the liquid state, preferably through fluidization over a short time period (e.g., less than or equal to 2 minutes) and with minimal cell juice temperature increase (e.g., less than or equal to 20° C.) during fluidization. The short fluidization period and low temperature rise minimize both denaturation and oxidative damage to the cell juice. This results in cell juice having essentially identical physiochemical and biochemical properties as those measured before freezing.

Cell juice includes three major types of components; (i) membrane bound chloroplasts, mitochondria, endoplasmic reticulum, nucleuses, lysosomes, peroxysomes, vacuoles, Golgi apparatus; and (ii) non membrane bound ribosomes, microtubules; and (iii) components which are not pertaining to the above groups, such as cytoplasm. Due to the presence in the cell juice of organelles and their fragments as well as unwanted pigments and proteins, fractionation is required to produce a personal care ingredient having a desirable combination of functional properties including but not limited to color, solubility, transparency, stability, and in vitro activities.

The cell juice is fractionated using various treatments including pH adjustments, focused microwave radiation, centrifugal separation, and vacuum filtration. The resulting isolated cell juice serum fraction is then stabilized with preservatives and anti-oxidants to produce the final ficus serum fraction.

The pH of the cell juice is adjusted to >3.0 (pH adjustment 1). In one embodiment, the cell juice pH, which is close to neutral (7.0), is adjusted using a titration method utilizing 5.0 N Hydrochloric Acid (HCl) to decrease the pH of the cell juice to ≥3.0 (pH adjustment 1).

Chlorophyll is then removed from the adjusted cell juice. Beside unwanted presence of this pigment in cosmetic ingredients, chlorophyll can be transformed to pheophorbides which are considered to be toxic compounds (Bergstrom, L. C., Vucenik, I., Hagen, I. K., Chernomorsky S. A., Poretz R. D. in-vitro photocytotoxicity of lysosomotropic immunoliposomes containing pheophorbide a with human bladder carcinoma cells.—J. Photochem, Photobiol., 24, 1, 17-23, 1994) and responsible for skin irritation (Kato T., Yamada K. Relationship between appearance of photosensitization and total pheophorbide level in spirulina powder.—J. Food Hyg. Soc. Japan, 36, 632-634, 1995).

In one embodiment, chlorophyll removal is achieved by heating then cooling the adjusted cell juice, followed by separation of the precipitate from the supernatant. In a particular embodiment, the adjusted cell juice is promptly treated by focused microwave radiation with frequency 2,450 MHz. During this Focused Microwave Processing (FMP) the cell juice temperature is momentarily increased to 90° C., held at this temperature for 1 minute and then the cell juice temperature is immediately decreased to ≤30° C. Then the treated cell juice is quickly separated using continuous flow centrifuge CEPA LE (Carl Padberg Zentrifugenbau GmbH, Germany) at 15,000 rpm and retention time of ≥30 seconds. The separation of treated cell juice yields green colored paste precipitate ("Precipitate I") and light brown colored slightly opalescent liquid supernatant ("Supernatant I"). This Supernatant I is used for further fractionation.

Supernatant I is further treated to significantly remove brown pigments and other unwanted compounds including residual proteins. This treatment includes pH adjustment and separation. The pH of Supernatant I is adjusted to increase the pH to about 7.5 (pH adjustment 2). In one embodiment, pH adjustment 2 is accomplished via a titration method utilizing 50% Sodium Hydroxide (NaOH) to increase the pH of cell juice Supernatant I from ~3.0 to ~7.5 (pH adjustment 2). The pH adjustment 2 results in darker color of material and developed opalescence which is then clarified via separation. In one embodiment, clarification is achieved via using continuous flow centrifuge CEPA LE (Carl Padberg Zentrifugenbau Germany) at 15,000 rpm and retention time of ≥30 sec. This separation results in a brown colored paste precipitate (Precipitate II) and a brown colored slightly opalescent supernatant (Supernatant).

Supernatant II is then pH adjusted (pH adjustment 3) and filtered. The pH of Supernatant II is adjusted to decrease the pH to about 3.6 (pH adjustment 3). In one embodiment, Supernatant II is subjected to titration utilizing 5.0 N Hydrochloric. Acid (HCl) to decrease the pH value to pH ~3.6 (pH adjustment 3). Such treatment leads to lighter color of titrated Supernatant II although its opalescence is slightly increased. The pH-adjusted Supernatant II is treated with sterilizing filtration through a membrane having the size of pores 0.2 micrometer. The resulting filtrate is a light colored transparent *Ficus* Serum Fraction (FSF). The FSF consists essentially of the *ficus* leaf cell cytoplasm.

Further stabilization of Serum Fraction can be achieved by adding antioxidants, stabilizers, chelating agents, and preservatives. In one embodiment, the following additives are added to the *Ficus* Serum Fraction: 0.2 sodium metabisulfite, 0.1% potassium sorbate, 0.1 sodium benzoate, and 0.1% sodium methyl paraben. In this embodiment, the mixture is incubated until complete solubilization of the additives is achieved (≥30 minutes). Then 1.9% pentylene glycol was added to the mixture.

FSF Properties

The resulting FSF demonstrates properties which make it desirable for use as a cosmetic ingredient. These properties include stability, water solubility, absence of undesirable materials such as pheophorbides and proteins, lighter color, higher solids content, and presence of higher levels of desirable compounds such as phenylalanine.

Stability studies indicate that cosmetic ingredients produced from FSF via these methods are stable at room temperature for at least 6 months. As used herein, "stable" means there is no significant change in physical or chemical properties of the composition over the specified period of time when stored in a dark, dry area at STP (standard temperature and pressure: 25° C., 1 atm). These properties include color and chemical composition. In some embodiments, the FSF and compositions comprising it are stable for at least 6 months, in others for at least 12 months, and in still others for at least 24 months. In particular embodiments, the compositions are stable for 6 to 24 months, from 12 to 24 months, or from 6 to 12 months.

Water Solubility

The FSFs of the present invention are also water soluble. As used herein, "water soluble" means that the FSF is miscible with water in any proportion (at STP). Because the FSF is water soluble, it allows for greater flexibility in formulating compositions comprising *ficus*. For instance, water-based formulations are often desired by consumers for their non-greasy feel, desirable spreadability, light skin-feel, and their ease of removal (e.g., rinsing) from skin surfaces.

Non-water soluble, traditional *ficus* extracts that have been extracted using solvents, however, can present formulation difficulties such as phase separation, settling out, crystallization, and non-uniformity of active concentration throughout the water-based composition. In order to overcome the formulation issues associated with non-water soluble actives, more complex formulations such as emulsions (which typically introduce oily and/or oily-feeling materials into the composition), are typically used. This leads to compositions having greasy, heavy, and/or tacky skin-feel, compositions that are not as easily removed from the skin surface, and more costly and/or complex manufacturing processes. In many instances, these formulations can also hinder the delivery of the active to the skin.

Because the FSF is fully water-soluble, however, it can be incorporated into water-based formulations without the afore-mentioned problems associated with non-water-soluble, traditional *ficus* extracts. This leads to greater formulation flexibility, thus enabling the delivery of *ficus* compositions having superior consumer-desired attributes.

Furthermore, because the FSF is fully water-soluble, it is more bioavailable than solvent extracts that are not fully water-soluble. This makes delivery of active components from the FSF to the skin more efficacious.

In addition, measuring many of the potential biological activities of traditional solvent extracts is not feasible due to their insolubility in water. For instance, it was not possible to measure IC50 values of solvent extracts in the present study since they were not water soluble.

Safety/Allergenicity

The FSF is also substantially free of pheophorbides and proteins, materials commonly found in plants, including *ficus*. These materials are known to create safety found in plants, these materials typically do not raise concern. However, when plant materials are concentrated, such as through processing, the relative concentration present dramatically increases and can create safety concerns. Accordingly, compositions not containing these materials are highly preferred.

Pheophorbides are pigment compounds that are chlorophyll degradation products, in addition to causing product discoloration, these pigments are also known to be biological toxins as well as skin photosensitizers. (Bergstrom, L. C., Vucenik, I., Hagen, I. K., Chernomorsky S. A., Poretz R. D. In-vitro photocytotoxicity of lysosomotropic immunoliposomes containing pheophorbide a with human bladder carcinoma cells.—J. Photochem. Photobiol., 24, 1, 17-23, 1994); (Kato T., Yamada K. Relationship between appearance of photosensitization and total pheophorbide level in spirulina powder.—J. Food Hyg. Soc. Japan, 36, 632 634, 1995).

Figure 2:
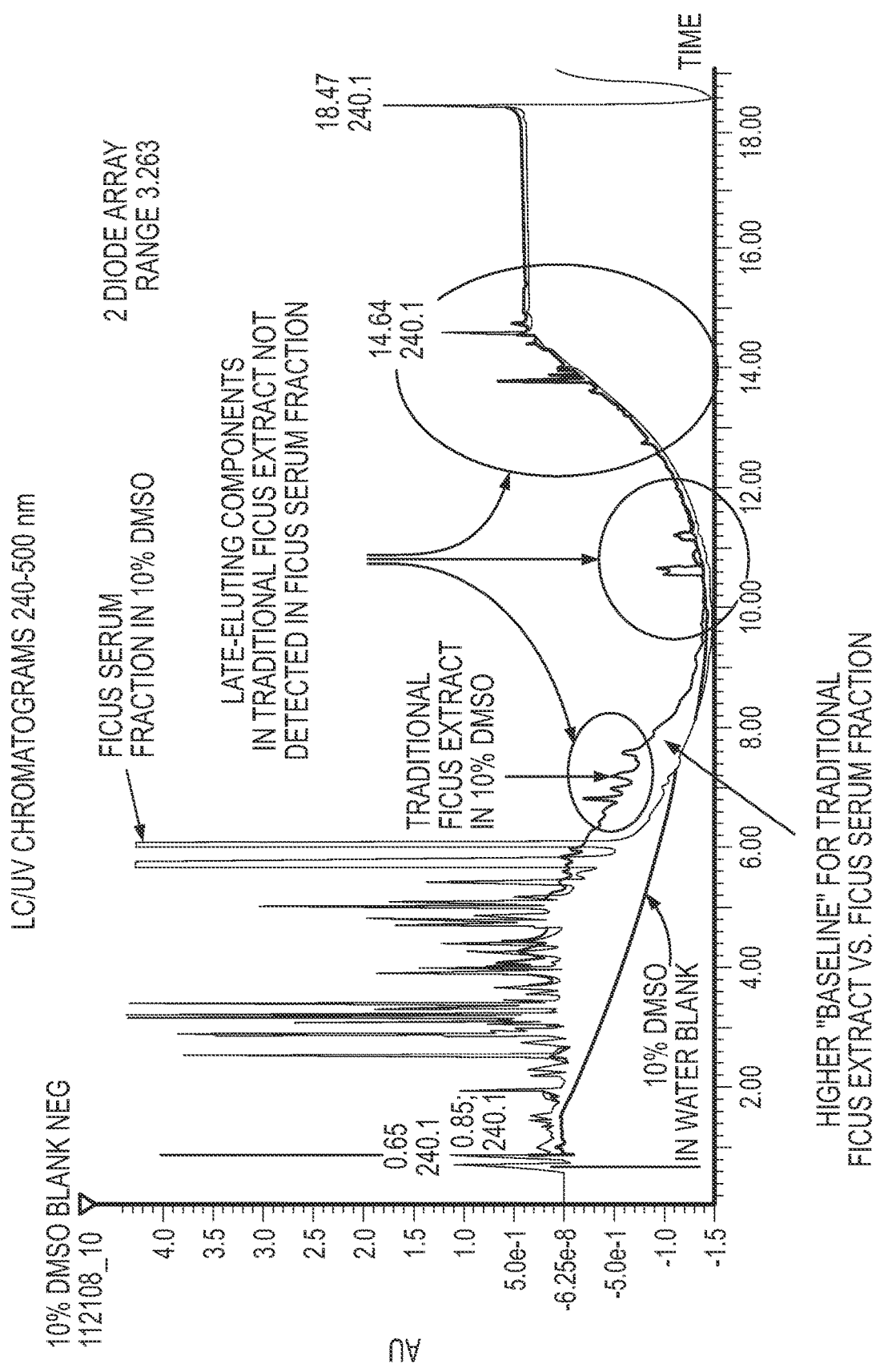
FIG. 2 is the LC/UV chromatogram of the traditional *ficus* extract superimposed upon that of the *ficus* serum fraction, showing that traditional extract contains higher levels of late-eluting (more hydrophobic) compounds that are not detected in the *ficus* serum fraction.
Figure 3:
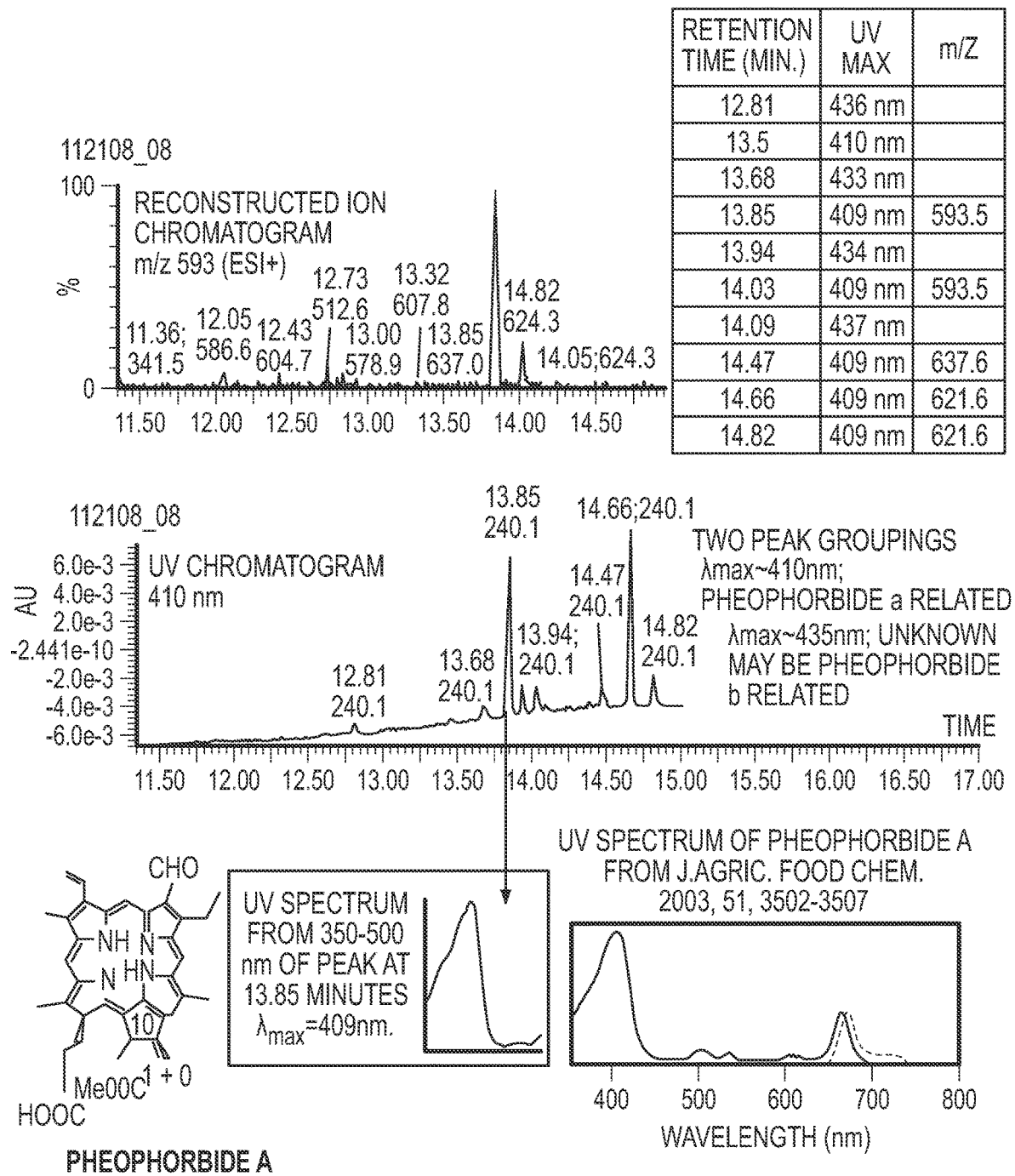
FIG. 3 is the LC/UV chromatogram of the traditional *ficus* extract's later eluting compounds and their corresponding extracted ion chromatogram, identifying them as pheophorbides, pigment compounds that are chlorophyll degradation products.

As shown in FIG. 2, traditional *ficus* extract of Example 3) contains late eluting (i.e. more hydrophobic) compounds that are not detected in the FSF (of Example 1). As shown in FIG. 3, a LC/UV chromatogram of the traditional *ficus* extract's later eluting compounds and their corresponding extracted ion chromatogram identified these compounds as pheophorbides. (See example 5).

Proteins, including those in plants such as *ficus*, can cause protein contact dermatitis in sensitive individuals. Shortly after contact with the causative proteinacous material, such individuals can experience symptoms such as acute urticarial or vesicular eruption on the skin, often accompanied by pruritus, burning, and/or stinging. (V. Janssens, et al., "Protein contact dermatitis: myth or reality?", British Journal of Dermatology 1995; 132: 1-6). Accordingly, it is highly desirable that skin care materials contain as little proteins as possible.

The FSF was tested for total protein content (Example 1, Table 3) using the Kjeldahl method. No protein was detected in the FSF. As used herein, "substantially free of proteins" means less than 1% (from 0% to 1%) total protein content using the Kjeldahl method. In some embodiments, protein content is from 0% to 1%, in others from 0% to 0.5%, and in others from 0% to 0.25% of the FSF.

Color/Color Stability

Figure 8:
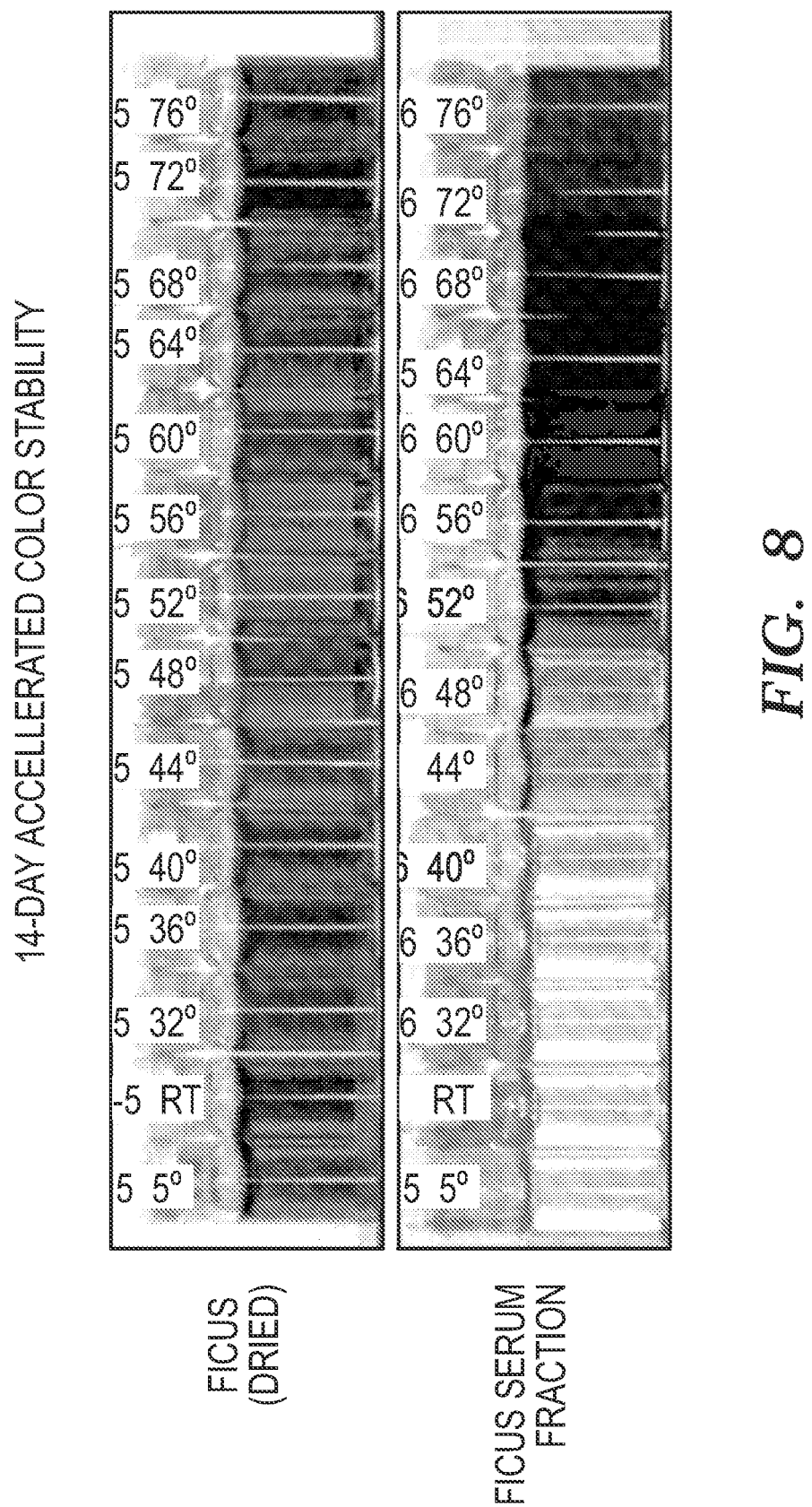
FIG. 8 is two color photographs from an accelerated aging study, showing the color stability of dry leaf *ficus* extract versus FSF. two different cosmetic compositions comprising different levels of *ficus* serum fraction and different preservatives.
Figure 9:
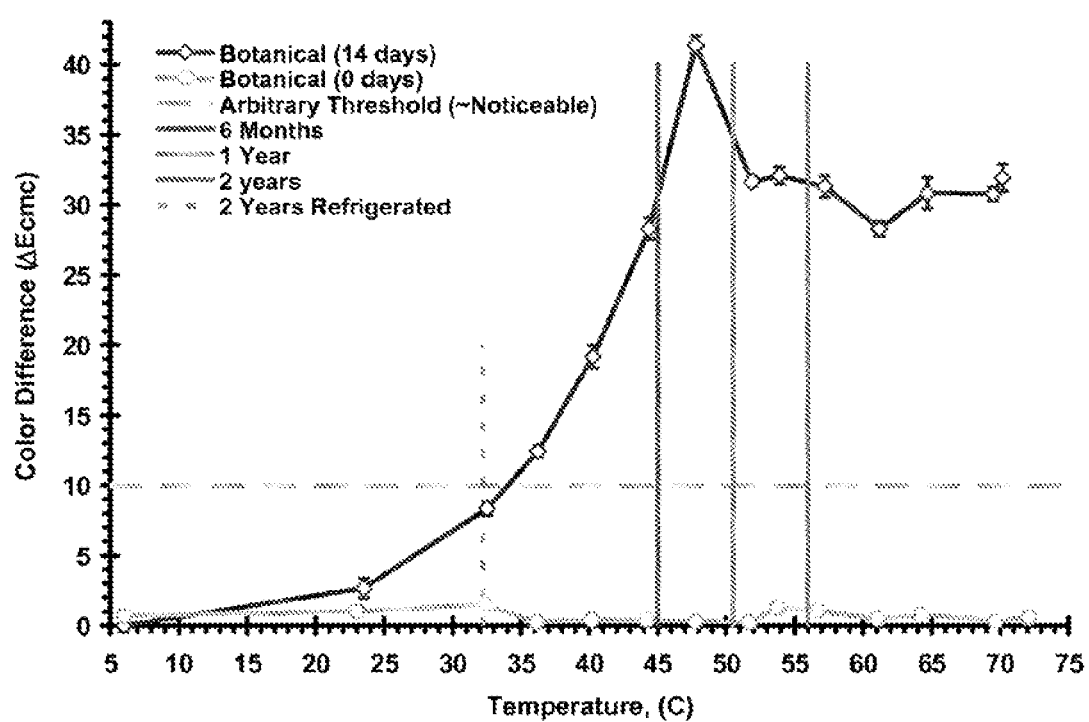
FIG. 9 is the calibration plot for the accelerated aging study of FIG. 8.
Figure 10:
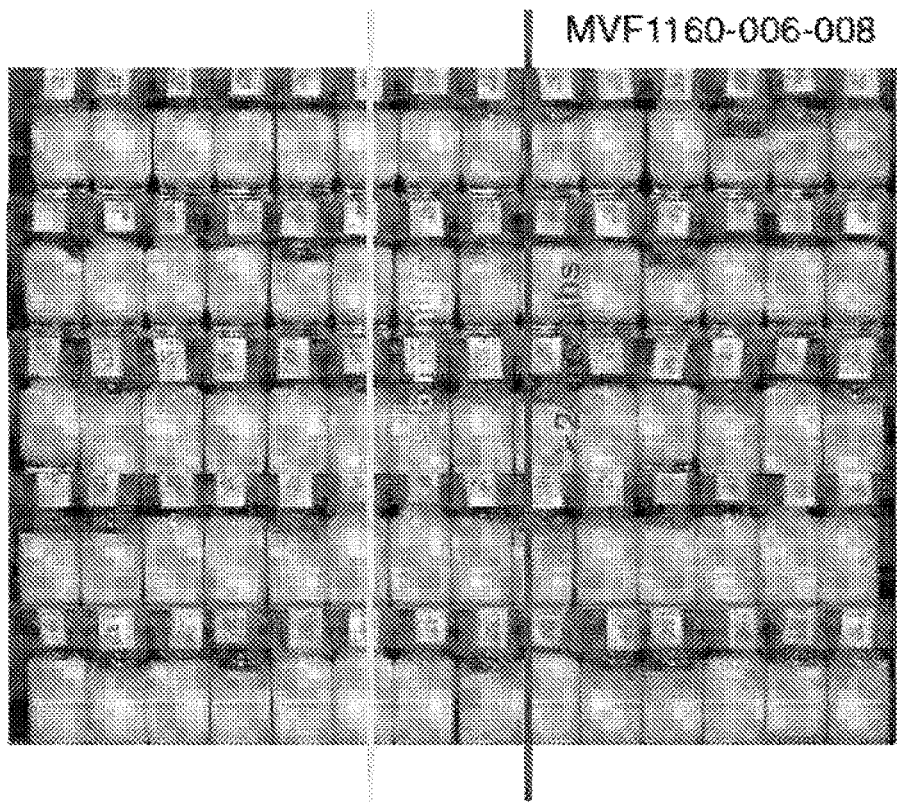
FIG. 10 is a color photograph from an accelerated aging study where a vehicle containing 0.55% FSF and various concentrations of preservative are compared.

The FSF has a lighter color than traditional *ficus* extracts. The FSF has a Gardner color value of less than 8, and in some embodiments less than 7.5. Particular from 6.5 to 8. FIG. 8 shows the color difference of FSF versus that of a dry leaf *ficus* extract in a 14-day accelerated aging study. FIG. 10 shows the color difference of 0.55% FSF in a vehicle having varying levels of stabilizer/preservative. FIG. 9 is the calibration chart constructed for the accelerated aging study analysis of FIG. 8.

Figure 4:
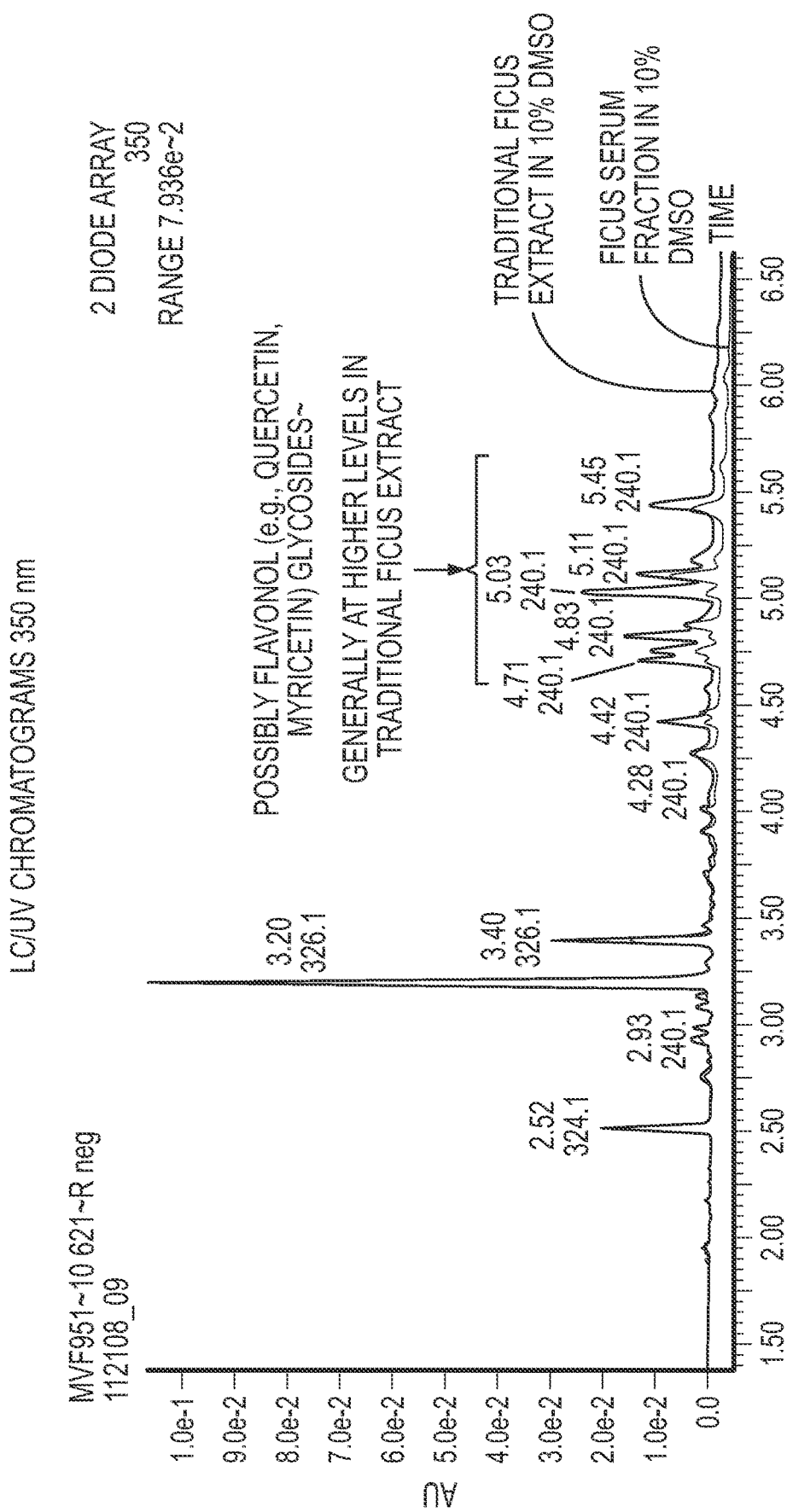
FIG. 4 is an LC/UV chromatogram of traditional *ficus* extract superimposed upon that of the *ficus* serum fraction, showing that traditional extract contains higher levels of flavonol glycosides.

The present investigators have identified several components of interest in traditional extract that are not present and/or are present at much lower levels in FSF that could account for the color and color stability differences between them. For instance, FIG. 4 shows that traditional extract contains higher amounts of what are likely flavonol glycosides. Flavonol glycosides can combine with tannins (which are found in both FSF and traditional extract) to form polymeric pigments. The higher level of flavonol glycosides could therefore lead to the formation of higher levels of pigment compounds in the traditional extract. Furthermore, the polyphenolic structure of flavonoids and tannins renders then quite sensitive to factors such as oxidation, heat, and light, which can potentially account for the increased presence of pigments in the traditional extract over time.

Solids Content

The solids contain the biologically active portion of the FSF or extracts. Thus, the higher the solids content the higher the botanical activity. The FSF has a higher solids content as compared to traditional water-soluble *ficus* extracts. The FSF has a solids (dry matter) content of greater than 5% by weight, and in particular embodiments from 5% to 20%, or from 5% to 10%, by weight the FSF.

FSF Bioactivity

FSF exhibits at least four different mechanisms of action recognized to regulate pigmentation production in the skin. These mechanisms are tyrosinase trypsin inhibition, COX-2 inhibition, and anti-oxidant activity. In one embodiment, the FSF has at least one of the following pigmentation reduction activities, in others at least two, and alternatively at least 3 of the following pigmentation reduction activities: tyrosinase inhibition IC50 (% DM) from 0.003 to 006; trypsin inhibition IC50 (% DM) from 0.02 to 0.5; COX-2 inhibition IC50 (% DM) from 0.02 to 1; and antioxidant super-oxide scavenging ability as measured by DPPH assay (1/x DM) from 1 to 15, and/or as measured by ORAC assay (1/x DM) from 0.2 to 5. As used herein, "DM" is dry matter ("solids"), "ORAC" is oxygen radical absorbance capacity, and "DPPH" is a measure of free radical scavenging ability.

Furthermore, as demonstrated by the B16 melanin suppression assay of Example 6, FSF is more effective at suppressing melanin production than the traditional *ficus* dry leaf solvent extract. For instance, at a concentration of 0.01, the FSF resulted in over twice the degree of melanin synthesis inhibition (48.1% melanin inhibition) than the traditional extract (23% melanin inhibition).

Accordingly, the present invention provides a method for regulating melanogenesis (i.e. melanin suppression) in the skin. Various forms of hyperpigmentation (e.g., freckles, age spots, liver spots, blotchiness, mottled pigmentation, and the like) involving concentration of melanin in the skin, are believed to result from changes in the melanocytes and the keratinocytes present in the epidermis. Melanocytes, which are located at the base of the epidermis, lose their normal regulation process with aging and produce excess pigment. This excess production leads to the formation of dense perinuclear clumps of melanin in keratinocytes within the epidermis, resulting in areas of hyperpigmentation.

Traditional therapy for hyperpigmented skin includes the application of certain skin lightening agents which inhibit melanin formation. A mechanism of action for these materials which has been proposed in the art is tyrosinase inhibition and/or it of other steps in melanin synthesis. Tyrosinase is present within the melanosomes in epidermal melanocytes and catalyzes the committed step in the formation of melanin from tyrosine. (See Goldsmith, L. A., PHYSIOLOGY, BIOCHEMISTRY, AND MOLECULAR BIOLOGY OF THE SKIN, Oxford University Press, pp. 873-903, N.Y. 1991). Tyrosinase catalyzes the hydroxylation of tyrosine and the oxidation of (DOPA to DOPA quinine. Binding of an inhibitor to the active site of tyrosinase thus results in decreased melanin formation. See generally Prota, G. Melanins and Melanogenesis, Academic Press, Inc., (San Diego 1992).

Oxidative processes are involved in the non-enzymatic steps of melanin production. The conversion of DOPA quinone to melanin occurs via non-enzymatic or spontaneous chemical reactions, some of which involve reactive oxygen species (ROS) or oxygen radicals. Oxidative stress on melanocytes, such as by stimulation of reactive oxygen/oxygen radical species (e.g., which can occur with UV or sunlight exposure) results in initiation of the melanin production pathway within the melanocytes. Various anti-oxidants/radical scavengers have been used to help disrupt these processes and thus achieve skin lightening benefits.

Arachidonic acid-derived metabolites are known to serve as potent inflammatory mediators in skin, particularly in response to environmental insults such as UV, smog, and other such irritants. In this pathway, membrane phospholipids are converted to arachidonic acid (AA) by phospholipase A2. Once formed, AA is utilized by one of two competing biological pathways; either the cyclooxygenase (COX) pathway or the 5-lipoxygenase pathway. The most relevant enzyme in COX inflammatory pathway is COX-2, which catalyzes the conversion of arachidonic acid into PGH2, a transitory molecule that is rapidly converted to prostaglandins such as PGE2. Prostaglandins are autocrines or paracrins that act as local messengers responsible for eliciting an inflammatory response at the site of stimulation.

Absorption of *Ficus* Serum Fraction into the skin inhibits COX-2, preventing arachidonic acid-derived metabolites from being converted to prostaglandins. The net effect is a reduction in the prostaglandin pool, both basal and induced. A reduction in prostaglandin levels leads to both a direct reduction in the inflammatory response as well as a reduction in all resulting downstream messenger activities. Two of these messenger activities include the activation of melanin synthesis in melanocytes and the inhibition of collagen production in fibroblasts.

Prostaglandins are known to stimulate melanocytes by increasing the amount of tyrosinase, an enzyme responsible for melanin production. The stimulation of melanocytes and the overproduction of melanin leads to hyperpigmentation, which is observed as the darkening of an area of skin. Discolorations caused by inflammation, termed post-inflammatory hyperpigmentation, therefore result from the direct stimulation of prostaglandins on melanocytes. A reduction in the production of prostaglandins, caused by *Ficus* Serum Fraction's inhibition of COX2, would result in less melanin production and more even-toned skin.

The prostaglandin $PGE_2$ has been shown to have a significant effect on reducing Type I and/or Type III collagen synthesis in a variety of cells, including human dermal fibroblasts, rat mesangial cells, and hepatic stellate cells [refs]. Since Type I and III are the predominant forms of collagen that make up the skin dermis, this supports that elevated levels of $PGE_2$ in response to inflammation would lead to the inhibition of collagen synthesis. AA and $PGE_2$ have been shown to have an inhibitory effect on collagen synthesis. The addition of naturally derived COX-2 inhibitors, including the omega-3 fatty acids EPA and DHA, were able to off-set the inhibition of collagen synthesis caused by PGE2, leading to a net increase in collagen synthesis. Therefore *Ficus* Serum Fraction likely improves skin texture by inhibiting COX 2, which reduces the formation of the prostaglandins that cause collagen inhibition.

It has been unexpectedly found that *ficus* serum fraction achieves superior skin lightening effects in comparison to traditional *Ficus* extract, including lightening of hyperpigmented regions in mammalian skin, when applied topically to the skin. Furthermore, analytical testing has shown that the *ficus* serum fraction of the present invention disrupts melanin synthesis via multiple mechanisms of action, affecting both enzymatic and non-enzymatic pathways. The FSF has enhanced bioactivity compared to traditional *Ficus* extract, including one of or a combination of enzyme inhibitory activities, free radical scavenging activity, antioxidant activity, and melanin synthesis inhibitory activity. Enzyme inhibitory activities include but are not limited to one of or a combination of tyrosinase, elastase, trypsin, and cyclooxygenase-2 ("COX-2") inhibitory activities. Antioxidant activity includes but is not limited to oxygen radical absorbance capacity.

Although the present investigators have also shown by way of example that traditional *ficus* extracts can deliver a hyperpigmentation benefit, these traditional extracts are not as efficacious and they have properties making them less suitable and thus less desirable for use in cosmetic compositions.

Figure 5:
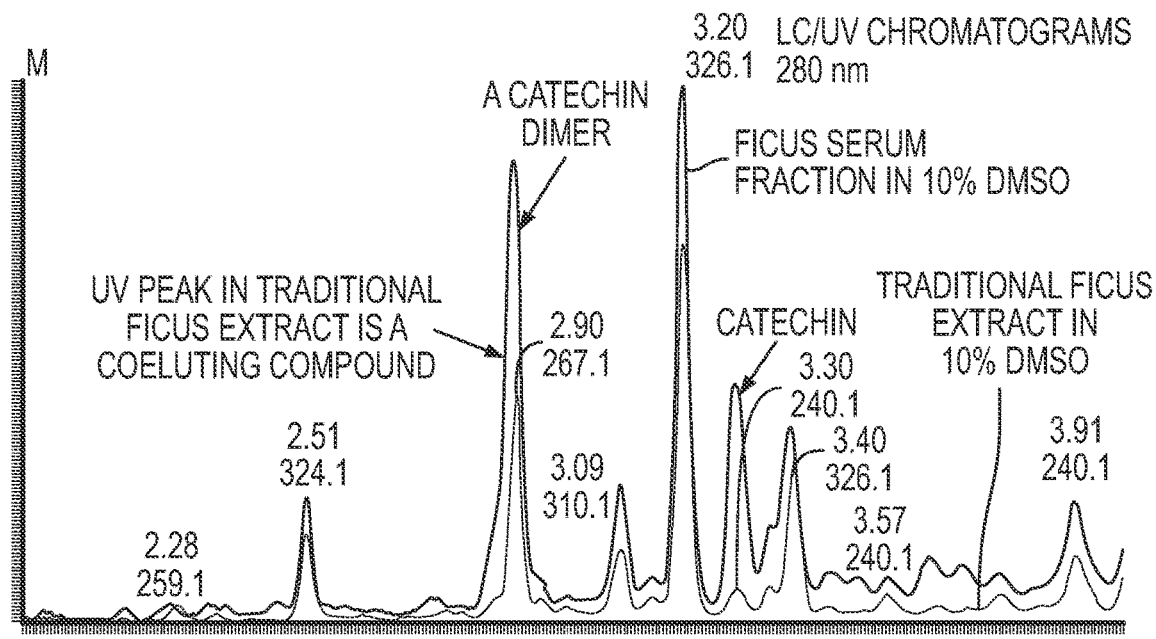
FIG. 5 is a portion of the traditional *ficus* extract LC/UV chromatogram and corresponding extracted ion chromatogram, superimposed upon that of the *ficus* serum.
Figure 5:
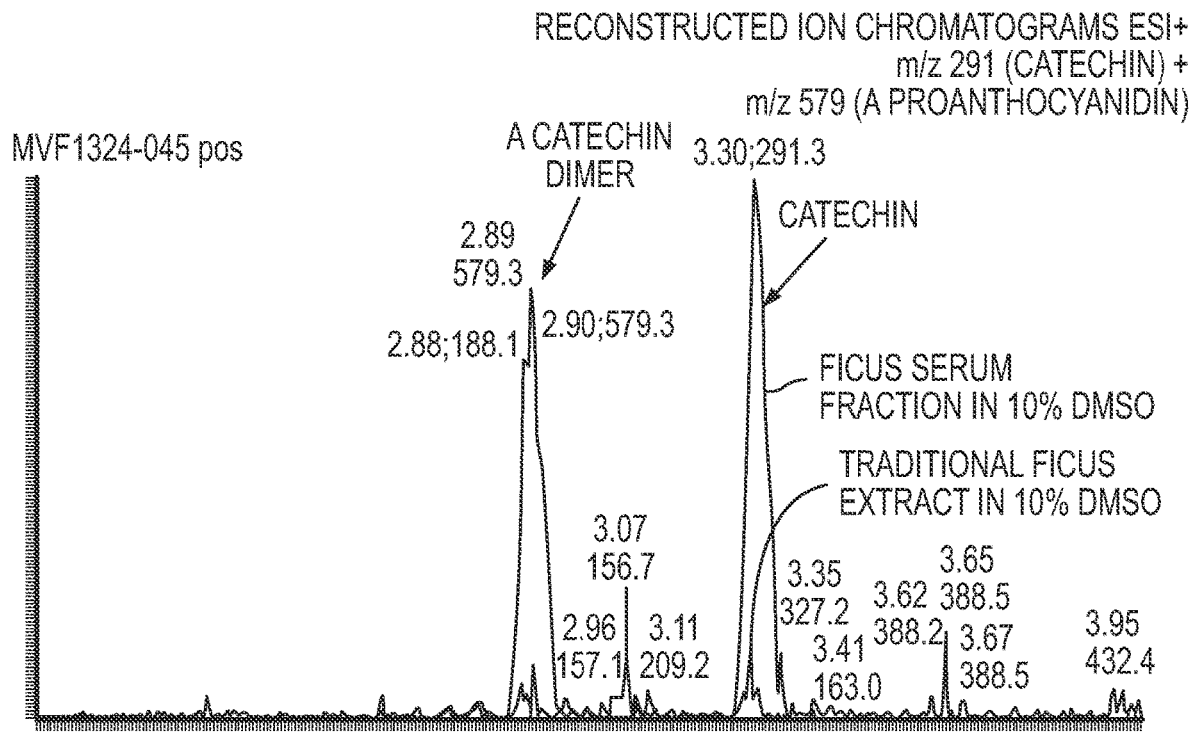
Figure 6:
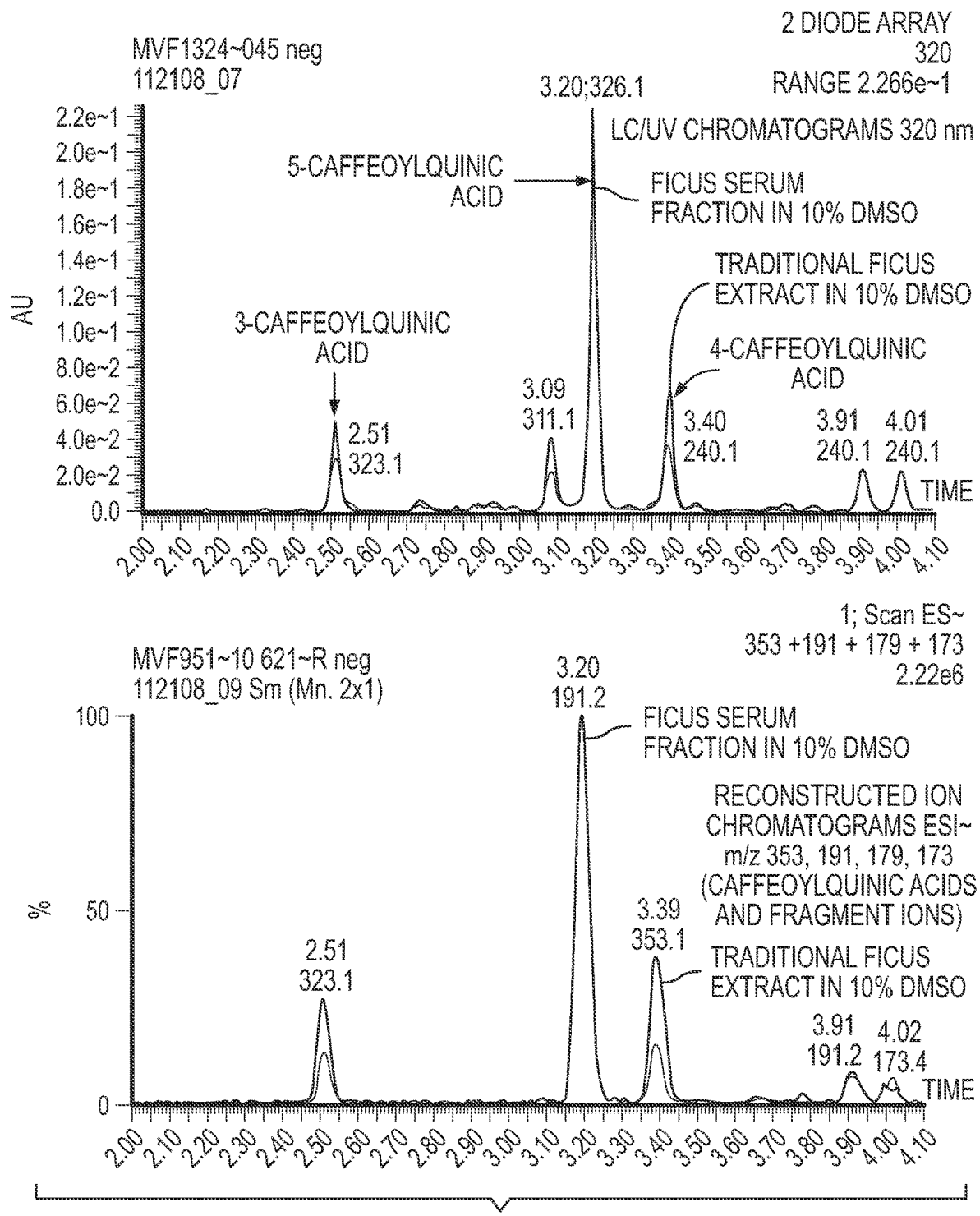
FIG. 6 is a portion of the traditional *ficus* extract LC/UV chromatogram and corresponding extracted ion chromatogram, superimposed upon that of the *ficus* serum fraction, showing that the levels of three caffeoylquinic acid isomers did not appear to be substantially different between the two samples.
Figure 7:
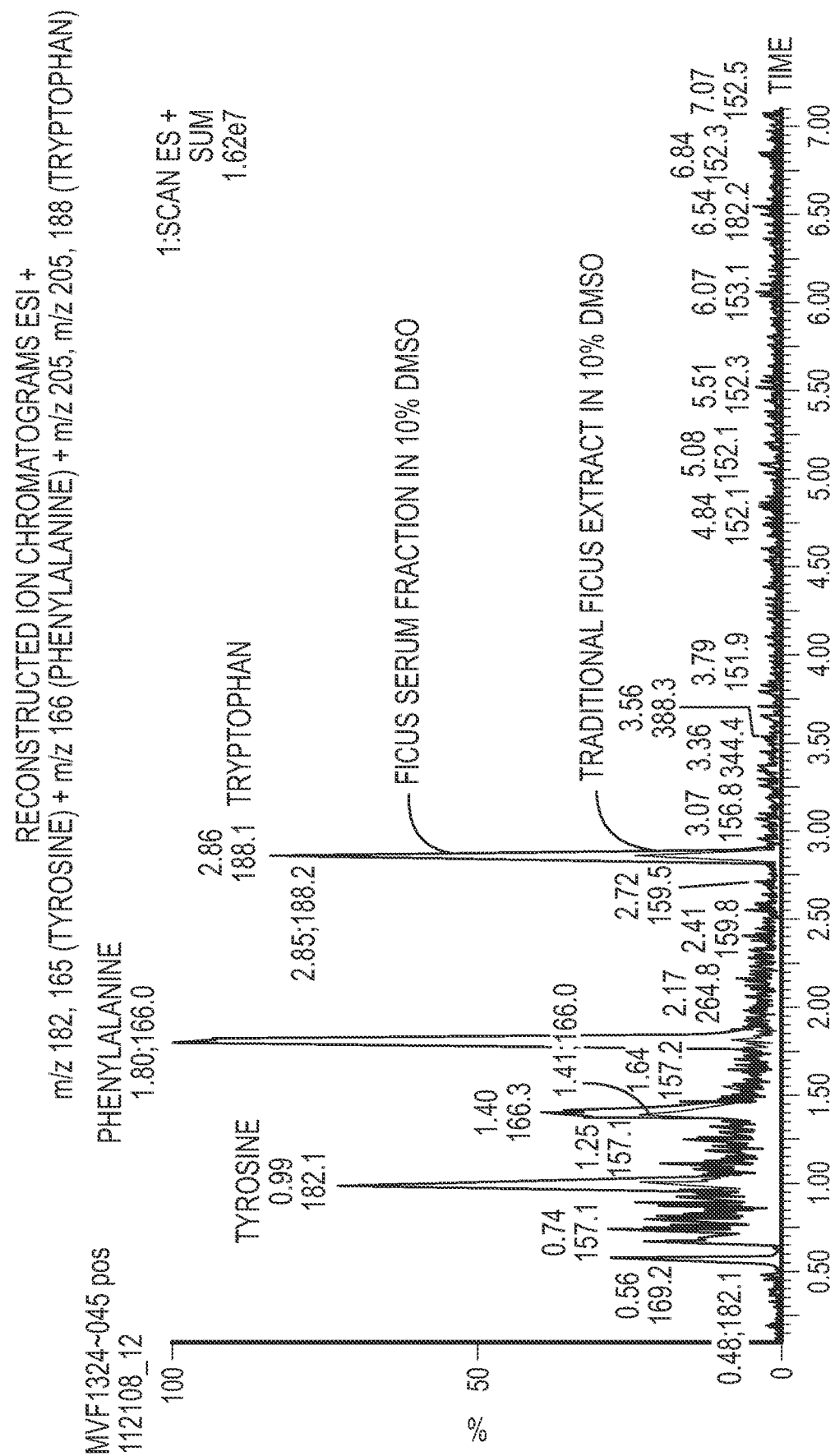
FIG. 7 is a portion of the traditional *ficus* extract LC/MS chromatogram superimposed upon that of the *ficus* serum fraction, showing that levels of free tyrosine, phenylalanine and tryptophan are higher in the *ficus* serum fraction.

As demonstrated in FIG. 5, the FSF has higher levels (by about 10×) of catechin and related condensed tannins. Condensed tannins (proanthocyanidins), such as catechins, are a class of flavanols. Proanthocyanidins are essentially polymer chains of flavonoids such as catechins. Tannins are believed to function as biological antioxidants (free radical scavengers) in the human body, and are widely believed to be effective in combating oxidative damage to skin, such as that caused by aging. Furthermore, antioxidants may help protect against the effects of internal and environmental stresses such as cigarette smoking and pollution, as well as supporting normal body metabolic processes. (Kehrer, J. P. Crit. Rev. Toxicol. 1993, 23, 21). FIG. 7 also demonstrates that FSF contained higher levels of free tyrosine, phenylalanine, and tryptophan which are essential amino acids. However, levels of the three caffeoylquinic acid isomers detected did not appear to be substantially different between the two samples, as demonstrated in FIG. 6.

B. Skin Tone Agent

In some embodiments, it may be desirable to include a skin tone agent in the composition in combination with the FSF. The skin tone agents can be included to further improve overall skin tone. When present, the compositions of the present invention contain up to about 50%, 40%, 30%, 20%, 10%, 5%, or 3%, by weight of the composition, of the skin tone agent. When present, the compositions of the present invention contain at least about 0.001%, 0.01%, 0.1%, 0.2%, 0.5%, or 1%, by weight of the composition, of the skin tone agent. Suitable ranges include any combination of the lower and upper limits including suitable ranges from about 0.1% to about 50%; from about 0.2% to about 20%; or from about 1% to about 10%, by weight of the composition, of the skin tone agent. The amounts listed herein are only to be used as a guide, as the optimum amount of the skin tone agent will depend on the specific active selected since their potency does vary considerably.

Suitable skin tone agents include, but are not limited to, sugar amines, vitamin B3 compounds, arbutin, deoxyarbutin 1,3-dihydroxy-4-alkylbenzene such as hexylresorcinol, sucrose dilaurante, bakuchoil (4-[(1E, 3S)-3-ethenyl-3,7-dimethyl-1,6 octadienyl] phenol or monterpene phenol), pyrenoine (available from Biotech Marine, France), panicum miliaceum seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *Helianthus annuus* (sunflower) and *Vitis vinifera* (grape) leaf extract, carnosine (i.e., dragosine), methyl gentisate, 1,2-hexanediol and 1,2-octandiol (i.e., combination sold as Symdiol 68 by Symrise AG, Germany), inositol, decylenoylphenylalanine (e.g., sold under the tradename Sepiwhite by Seppic, France), koijic acid, hexamidine compounds, salicylic acid, and retinoids retinol and retinyl propionate.

In certain embodiments, the additional skin tone agent, is selected from vitamin B3 compounds, sugar amines, hexamidine compounds, salicylic acid, 1,3-dihydroxy-4-alkylbenzene such as hexylresorcinol, and retinoids. As used herein, "vitamin $B_3$ compound" means a compound having the formula:

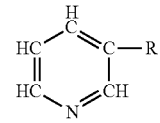

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. As used herein, "sugar amine" includes isomers and tat/tot/lets of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "hexaminide compound" means a compound having the formula:

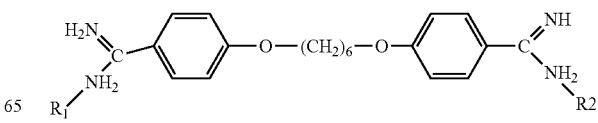

wherein R1 and R2 are optional or are organic acids (e.g., sulfonic acids, etc.). In one embodiment, hexamidine compound is hexamidine diisethionate.

C. Anti-Inflammatory Agents

Hyperpigmentation may result from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions of the present invention an anti-inflammatory agent. When present, the compositions of the present invention contain up to about 20%, 10%, 5%, 3%, or 1% by weight of the composition, of the anti-inflammatory agent. When present, the compositions of the present invention contain at least about 0.001%, 0.01%, 0.1%, 0.2%, 0.3%, 0.5%, or 1%, by weight of the composition, of the anti-inflammatory agent. Suitable ranges include any combination of the lower and upper limits. Suitable anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol (e.g., alpha bisabolol), manjistha (extracted from plants in the genus *Rubia*, particularly *Rubia cordifolia*), and guggal (extracted from plants in the genus *Commiphora*, particularly. *Commiphora mukul*), kola extract, chamomile, red clover extract, and sea whip extract (extracts from plant in the order Gorgonacea), derivatives of any of the foregoing, and mixtures thereof.

D. Sunscreen Actives

The compositions of the subject invention may comprise one or more sunscreen actives (or sunscreen agents) and/or ultraviolet light absorbers. Herein, "sunscreen active" collectively includes, sunscreen actives, sunscreen agents, and/or ultraviolet light absorbers. Sunscreen actives include both sunscreen agents and physical sunblocks. Sunscreen actives may be organic or inorganic. Examples of suitable sunscreen actives are disclosed in Personal Care Product Council's *International Cosmetic Ingredient Dictionary and Handbook*, Thirteenth Edition, as "sunscreen agents." Particularly suitable sunscreen actives are 2-ethylhexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)aminobenzoate, 2-ethylhexyl-2-cyano-3,3-diphenylacrylate 2-ethylhexyl-salicylate, glyceryl-p-aminobenzoate, 3,3,5-tri-methylcyclohexylsalicylate, menthyl anthranilate, p-dimethyl-aminobenzoic acid or aminobenzoate, 2-ethylhexyl-p-dimethyl-aminobenzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In one embodiment, the composition may comprise from about 1% to about 20%, and alternatively from about 2% to about 10% by weight of the composition, of the sunscreen active. Exact amounts will vary depending upon the chosen sunscreen active and the desired Sun Protection Factor (SPF), which is within the knowledge of one of skilled in the art.

E. Optional Components

The compositions of the present invention ma contain a variety of other ingredients provided that they do not unacceptably alter the benefits of the invention. When present, compositions of the present invention may contain from about 0.0001% to about 50%; from about 0.001% to about 20%; or, alternately, from about 0.01% to about 10%, by weight of the composition, the optional components. The amounts listed herein are only to be used as a guide, as the optimum amount of the optional components used in a composition will depend on the specific active selected since their potency does vary considerably. Hence, the amount of some optional components useful in the present invention may be outside the ranges listed herein.

The optional components, when incorporated into the composition, should be suitable for use in contact with human skin tissue without undue toxicity, incompatibility, instability, allergic response, and the like. The compositions of the present invention may include optional components such as anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives, which are described in further detail in U.S. application publication No. US2006/0275237A1 and US2004/0175347A1.

The Personal Care Product Council's International Cosmetic Ingredient Dictionary and Handbook, Thirteenth Edition, describes a wide variety of non-limiting cosmetic and pharmaceutical ingredients commonly used in the skin care industry, which are suitable optional components for use in the compositions of the present invention. Examples of these ingredient classes include: abrasives, absorbents, aesthetic components such as fragrances, pigments, colorings/colorants, essential oils, anti-caking agents, antifoaming agents, antimicrobials, binders, biological additives, buffering agents, bulking agents, chelating agents, chemical additives, colorants, cosmetic astringents, cosmetic biocides, denaturants, drug astringents, emollients, external analgesics, film formers or materials, opacifying agents, pH adjusters, preservatives, propellants, reducing agents, sequestrants, skin cooling agents, skin protectants, thickeners viscosity modifiers, vitamins, and combinations thereof.

F. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oily). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e., less than 1% water) or fully anhydrous.

A suitable carrier is selected to yield a desired product form. Furthermore, the solubility or dispersibility of the components (e.g., FSF, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and *McCutcheon's Detergents and Emulsifiers*, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

G. Exemplary Compositions

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

All Examples may be used to treat or improve the appearance of one or more hyperpigmented spots. The present invention may further relate to a regimen involving the localized treatment for one or more hyperpigmented spots by a first composition (e.g., Examples A or B) and a more broad or general facial skin treatment by a second composition (e.g., Examples C, D, and E), which can be applied before or after the localized treatment to improve skin tone across the face.

| Component | Ex. A | Ex. B | Ex. C | Ex. D | Ex. E |
|---|---|---|---|---|---|
| *Ficus* Serum Fraction | 0.55 | 1.000 | 1.000 | 1.000 | 1.000 |
| N-Acetylglucosamine | 0 | 0 | 2.000 | 0 | 0 |
| Hexamidine Diisethionate | 0 | | | 0.090 | 0.090 |
| Undecylenoyl-phenylalanine *2 | 0 | 1.000 | 0.500 | 0 | 0 |
| Dipotassium Glycyrrhizate | 0 | 0.300 | 0.100 | 0.100 | 0.100 |
| Niacinamide | 5.000 | 5.000 | 5.000 | 5.000 | 5.000 |
| Isohexadecane | 3.000 | 3.000 | 3.000 | 3.000 | 3.000 |
| Isopropyl isostearate | 1.330 | 1.330 | 1.330 | 1.330 | 1.330 |
| Sucrose polycottonseedate | 0.670 | 0.670 | 0.670 | 0.670 | 0.670 |
| Polymethyl-silsesquioxane | 0.250 | 0.250 | 0.250 | 0.250 | 0.250 |
| Cetearyl glucoside + cetearyl alcohol *3 | 0.200 | 0.200 | 0.200 | 0.200 | 0.200 |
| Behenyl alcohol | 0.400 | 0.400 | 0.400 | 0.400 | 0.400 |
| Cetyl alcohol | 0.320 | 0.320 | 0.320 | 0.320 | 0.320 |
| Stearyl alcohol | 0.480 | 0.480 | 0.480 | 0.480 | 0.480 |
| Tocopheryl acetate | 0.500 | 0.500 | 0.500 | 0.500 | 0.500 |
| PEG-100 stearate | 0.100 | 0.100 | 0.100 | 0.100 | 0.100 |
| Glycerin | 7.000 | 7.000 | 7.000 | 7.000 | 7.000 |
| Titanium dioxide | 0.604 | 0.604 | 0.604 | 0.604 | 0.604 |
| Polyacrylamide + C13-14 isoparaffin + laureth-7 *4 | 2.000 | 2.000 | 2.000 | 2.000 | 2.000 |
| Allantoin | 0.200 | 0.200 | 0.200 | 0 | 0 |
| Panthenol | 1.000 | 1.000 | 1.000 | 1.000 | 1.000 |
| Disodium EDTA | 0.100 | 0.100 | 0.100 | 0.100 | 0.100 |
| Benzyl alcohol | 0.400 | 0.400 | 0.400 | 0.400 | 0.400 |
| Dimethicone/Dimethiconol *5 | 2.000 | 2.000 | 2.000 | 2.000 | 2.000 |
| Homosalate | 0 | 0 | 0 | 0 | 9.000 |
| Avobenzone | 0 | 0 | 0 | 0 | 3.000 |
| Octocrylene | 0 | 0 | 0 | 0 | 2.600 |
| Oxybenzone | 0 | 0 | 0 | 0 | 1.000 |
| Octisalate | 0 | 0 | 0 | 0 | 4.500 |
| Water | QS | QS | QS | QS | QS |
| TOTAL | 100 | 100 | 100 | 100 | 100 |

*1 - Produced by Integrated Botanical Technologies, New York.
*2 - Sepiwhite available from SEPPIC, France.
*3 - Emulgade PL 68/50 available from Cognis GmbH.
*4 - Sepigel 305, available from SEPTIC, France.
*5 - Dow Corning DC1503 available from Dow Corning, Inc., Midland, MI.

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by, first mixing the aqueous phase materials separately from the fatty phase materials and then combining the two phases as appropriate to yield the desired continuous phase. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Compositions of this invention preferably contain from or about 0.01% to or about 10%, of *ficus* serum fraction, more preferably from or about 0.05% to or about 5%, most preferably from or about 0.1% to or about 5%, e.g., 2%, *ficus* serum fraction.

H. Methods for Lightening Skin

The compositions of the present invention are useful for lightening mammalian skin (especially human skin, more especially facial and hand skin). The compositions are especially useful for lightening hyperpigmented regions of skin.

The method of lightening skin (including hyperpigmented regions) involves topically applying to the skin a safe and effective amount of a composition of the present invention, in one embodiment, cosmetic compositions of this invention can comprise from 0.01% to 10%, of *ficus* serum fraction. The amount of the composition which is applied, the frequency of application and the period of use will vary widely depending upon the level of *ficus* serum fraction and/or other components of a given composition and the level of lightening desired, e.g., in light of the level of skin pigmentation present in the subject and the rate of further skin pigmentation.

In a preferred embodiment, the composition is chronically applied to the skin. By "chronic topical-application" is meant substantially continuous topical application of the composition over an extended period during the subject's lifetime, preferably for a period of at least about one week, more preferably for a period of at least about one month, even more preferably for at least about three months, even more preferably for at least about six months, and still more preferably for at least about one year. While benefits are obtainable after various maximum periods of use (e.g., two, five, terror twenty years), it is preferred that chronic application continue throughout the subject's lifetime. Typically applications would be on the order of about once or twice per day over such extended periods, however application rates can vary, e.g., from about once per week up to about three times per day or more.

A wide range of quantities of the compositions of the present invention can be, employed to provide a skin lightening benefit. Quantities of the present compositions which are typically applied per application are from about 0.1 mg/cm2 skin to about 10 mg/cm2 skin. A particularly useful application amount is about 2 mg/cm2 skin.

The term "topical application", as used herein, means to apply or spread the compositions of the present invention onto the surface of the skin. Preferred compositions of the present invention are those in a form intended to be left in contact with the skin for an extended period (e.g., for several hours) after topical application, e.g., typical usage of a cream, lotion, moisturizer or the like.

The method of lightening skin is preferably practiced by topically applying a composition in the form of a skin lotion, cream, cosmetic, or the like which is intended to be left on the skin for some esthetic, prophylactic, therapeutic or other benefit. After applying the composition to the skin, it is preferably left on the skin for a period of at least about 15 minutes, more preferably at least about 30 minutes, even more preferably at least, about 1 hour, most preferably for at least several hours, e.g., up to about 12 hours.

The compositions of the present invention are also useful for regulating mammalian skin condition more generally (especially human skin, more especially facial and/or hand skin), including signs of skin aging, and visible and/or tactile discontinuities in skin associated with skin aging. Such regulation includes prophylactic and/or therapeutic regulation. Regulating skin condition involves topically applying to the skin a safe and effective amount of a composition of the present invention. The amount of the composition which is applied, the frequency of application and the period of use will vary widely depending upon the level of *ficus* serum fraction and/or other components of a given composition and the level of regulation desired e.g., in light of the level of skin aging present in the subject and the rate of further skin aging.

I. *Ficus* Serum Fraction Bio-Activity

The invention also relates to methods for reducing the appearance of skin hyperpigmentation by topically applying the cosmetic composition to hyperpigmented areas in order to disrupt one or more steps in melanogenesis (melanin synthesis). The cosmetic composition effects enzyme inhibition (trypsin inhibitory activity and/or tyrosinase inhibitory activity), anti-oxidant activities (ORAC and DPPH), and/or COX-2 inhibition, thereby disrupting one or more steps in melanogenesis.

The method for preparing bioactive botanical cosmetic compositions is advantageous over the methods currently available in that it yields plant extracts that capture the full spectrum of activity contained in the plant cells. As shown in Example 6, the *Ficus* extract of the present invention has much higher bioactivity than *Ficus* extracted via traditional means.

In one embodiment of the present invention, the method of lightening the skin of a mammal comprises topically administering a cosmetic composition comprising an effective amount of *Ficus* serum fraction to inhibit trypsin activity.

Another embodiment of the present invention comprises a method of lightening the skin of a mammal by inhibiting tyrosinase activity in the skin of a mammal, the method comprising topically administering to a mammal a cosmetic composition comprising an effective amount of *ficus* serum fraction.

Normal skin color is formed by melanin, a natural pigment that also determines hair and eye color. In the skin, the enzyme tyrosinase is essential to the biochemical pathway responsible for the conversion of the amino acid tyrosine into melanin. Hyperpigmentation occurs when too much melanin is produced and forms deposits in the skin. The cells that make pigment are called melanocytes. They are located at the base of the epidermis. Melanocytes produce melanosomes, which are passed onto other cells of the epidermis and make their way up to the top layer of skin. Synthesis of melanin occurs exclusively in melanosomes. When too much melanin is produced, deposits are formed and hyperpigmentation appears in the skin.

Tyrosinase is a copper-containing monooxygenase catalyzing the o-hydroxylation of monophenols to the corresponding catechols (monophenolase or cresolase activity), and the oxidation of monophenols to the corresponding o-quinones (diphenolase or catecholase activity). These functions of tyrosinase play an important role in the formation of melanin pigments during melanogenesis. Melanin production is principally responsible for skin color and plays an important role in prevention of sun-induced skin injury. However, abnormal accumulation of melanin products in skin is responsible for hyperpigmentations including melasma, chloasma, freckles, and senile lentigines, which can lead to an undesired aesthetic appearance (Jeon et al. (2005) Bull. Korean Chem. Soc, Vol. 26: 1135-1 137).

The invention relates generally to inhibiting the activity of at least one enzyme responsible for pigmentation or coloring of the skin within the skin tissue of a mammal. *Ficus* serum fraction can inhibit the activity of trypsin as well as tyrosinase and other tyrosinase-like enzymes. Furthermore, the invention relates effecting pigment-related antioxidant activity (ORAL and DPPH), including superoxide scavenging activity, as well as COX-2 inhibition.

The Serum-Derived Cosmetic Composition has a superoxide scavenging potency ranging from an ICR50 value of between about 50 and 190 μg of dry matter/ml. As used in the present application, the term "ICR50 value" represents the concentration of dry matter contained in the cell serum fraction required to inhibit 50 percent of cytochrome c reduction.

The compound can be administered to a mammal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

J. Optional Components

The compositions of the present invention may contain a variety of other ingredients that are conventionally used in given product types provided that they do not unacceptably alter the benefits of the invention. The composition may include a dermatologically acceptable carrier.

The optional components, when incorporated into the composition, should be suitable for use in contact with human skin tissue without undue toxicity, incompatibility, allergic response, and the like within the scope of sound judgment. The *CTFA Cosmetic Ingredient Handbook, Second Edition* (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, anti-caking agents, antifoaming agents, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, and thickeners.

In some embodiments, it may be desirable to include a second, third or fourth skin tone agent in the composition in combination with the FSF. The second, third, or fourth skin tone agents can be included to further improve overall skin tone. When present, the compositions of the present invention preferably contain from about 0.1% to about 50%, more preferably from about 0.2% to about 20%, even more preferably from about 1% to about 10%, by weight of the composition, of the additional skin tone agent. The amounts listed herein are only to be used as a guide, as the optimum amount of the additional skin tone agent will depend on the specific active selected since their potency does vary considerably. Preferred skin tone agents include, but are not limited to, N-acetylglucosamine, vitamin B3, and undecyle-noylphenylalanine (e.g., sold under the tradename Sepiwhite, Seppic, France). In some embodiments, one composition (e.g., composition #1 in Table #1) may be used as a localized treatment for one or more hyperpigmented spots while one or more other compositions (e.g., compositions #2, #3, and #4 in Table #1) can be applied before or after the specialized treatment more broadly to facial skin surfaces to improve skin tone across the face.

The topical compositions of the present invention can be provided in a variety of forms, including but not limited to lotions, milks, mousses, serums, sprays, aerosols, foams, sticks, pencils, gels, creams and ointments. In one embodiment, the composition is in the form of a solution and in another embodiment the composition is in the form of a lotion.

K. Composition Preparation

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g. appropriate dispersing agents or dual compartment packaging), use of appropriate photostability approaches (e.g., incorporation of sunscreen/sunblock, use of opaque packaging), etc.

L. Methods of Treatment

In one embodiment, a user selects a hyperpigmented spot for treatment and a first composition is applied to the hyperpigmented spot at least once a day, and more preferably twice a day, for at least about 4 weeks. In another embodiment the first composition is applied to the selected hyperpigmented spot for a period of at least about 8 weeks. The first composition can be in any form. In one embodiment, the composition is in the form of a solution that is applied with an eye dropper locally to the hyperpigmented spot. Other applicators that can apply the first composition locally to the hyperpigmented spot may be used. For example, a foam or cotton tipped applicator that releasably holds a first composition, such as a solution, lotion, or other form described herein, can be used for applying the composition to the hyperpigmented spot. In another embodiment, the composition is applied to the one or more hyperpigmented spots and more generally to one or more facial skin surfaces contemporaneously (i.e., within the same treatment cycle).

In some instances, the method of treatment comprises selecting a plurality of hyperpigmented spots for localized treatment by the first composition in one treatment cycle. As used herein a treatment cycle refers to a single application of a composition to the intended skin surface. For example, a single application of the first composition to one or more hyperpigmented spots in reasonably short succession (e.g., over a period of 1 to 30 minutes) would constitute a single treatment cycle. In contrast, a single application of the first composition to one or hyperpigmented spots twice a day constitutes two treatment cycles, wherein the applications are separated from each other by a longer time period (e.g., separated by 1 to 12 hours).

In one embodiment, the treatment method comprises application of a first composition in combination with a second composition that is applied before or after the first composition, wherein the second composition is applied more generally to one or more facial skin surfaces to improve the overall tonal appearance of the facial skin. The second composition can be applied to one or more of the forehead, perioral, chin, periorbital, nose, and cheek skin surfaces. In one embodiment, the second composition is applied contemporaneously to at least the cheek, forehead, and chin/perioral skin surfaces in a single treatment cycle. Given the larger surface area to which the second composition is applied compared to the localized treatment of the hyperpigmented spot.

While some methods described herein contemplate applying the compositions of the present invention with an applicator, it will be appreciated that applicators are not required and the compositions of the present invention can also be applied directly or using one's finger (or in some other manner). Further, while one embodiment of the present invention contemplates applying a composition locally to a hyperpigmented spot, it will be appreciated that compositions of the present invention can be applied more.

The following Examples are provided to illustrate certain features and advantages of various embodiments of the invention and should not be construed as limiting the scope thereof.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Preparation of Bioactive Serum Fraction Derived from Fresh Leaves of *Ficus benghalensis*

FIG. 1 is a schematic drawing demonstrating one embodiment of the process for preparing the bioactive serum fraction from fresh *ficus* leaves.

Sufficient amount of fresh *Ficus benghalensis* leaves were collected to yield approximately 100 kg of dry matter. The level of dry matter in the fresh leaves was measured to be 32.01%, requiring harvesting of approximately 312.4 kg of fresh plant leaves to yield 100 kg of dry matter. Care was taken to preserve the inherent moisture content of fresh leaves and to avoid wilting due to moisture loss. The collection was conducted in such a manner to avoid or minimize any damage to the collected fresh leaves. All steps were completed in the shortest possible period of time to minimize exposure of the fresh leaves to sun, high temperature, and other negative environmental factors.

The collected leaves were then washed for ≤5 minutes and ≤1 kg/cm2 water pressure to remove soil particles and other debris from the leaves prior to further processing. The residual water wash did not contain any green or brown pigments, indicating integrity of leaf tissue, proper water pressure and washing duration. The excess water was removed from the washed leaves. The washed fresh *ficus* leaves were then mechanically separated which effectively separated fiber free cell juice containing most of intracellular material of parenchyma cells from fiber enriched material, which predominately contains cell walls. No exogenous solvents or water was added prior or during the separation process.

The washed leaves underwent grinding, maceration, and pressing to obtain the liquid intracellular content (i.e. the cell juice) and to separate it from fiber enriched material. A hammer mill (Model VS 35, Vincent Corporation, Tampa, Fla.) having 5 HP engine and a set of screens was used to grind the leaves to yield leaf tissue particles of suitably small size in a shortest amount of time and without significant increase of biomass temperature. The hammer mill was set to produce the maximum size of macerated leaf particles of ≤2.0 centimeters during ≤10 seconds of treatment. The temperature of macerated fresh leaves was increased by only ≤2° C.

A horizontal continuous screw press (Compact Press CP-6, Vincent Corporation, Tampa, Fla.), equipped with a cone supported by compressed air, was immediately used to obtain cell juice from macerated fresh leaves. The pressure on the cone was maintained at a level of ≥15 g/cm2, with a screw speed of 12 rpm. At these conditions the temperature of the cell juice was increased only ≤5° C.

This treatment yielded fiber enriched material and cell juice. The residual small fiber particles were additionally removed from cell juice by clarification using a continuous flow centrifuge (Model 12-413V, AML Industries, Inc., Hatboro, Pa.) with full-automatic discharge unit. At flow rate of 2 liter/min, retention time for cell juice clarification at ≤2,250 g was ≥100 seconds. The above regimen produced fiber free cell juice. The precipitate containing small fiber particles was collected and combined with rest of fiber enriched material, which was produced after pressing of fresh leaves.

Processes described above allowed for the production of 160.9 kg of cell juice having dry mater content 9.29% and 151.5 kg of fiber enriched material having dry matter content 56.14%. The cell juice was promptly placed in tightly closed 15 liter rectangular HDPE containers and frozen at −30° C. Solid state frozen cell juice was kept at this low temperature for further utilization.

Cell juice includes three major types of components: (i) membrane bound chloroplasts, mitochondria, endoplasmic reticulum, nucleuses, lysosomes, peroxysomes, vacuoles, Golgi apparatus; and (ii) non membrane bound ribosomes microtubules; and (iii) components which are not pertaining to the above groups, such as cytoplasm. Due to the presence in the cell juice of organelles and their fragments as well as unwanted pigments and proteins, its fractionation was required to produce a personal care ingredient having a desirable combination of functional properties including but not limited to color, solubility, transparency, stability, and in vitro activities. To achieve these objectives, the cell juice was fractionated using various treatments including cell juice fluidization, pH adjustments, focused microwave radiation, centrifugal separation and vacuum filtration. Isolated cell juice serum faction was then stabilized with preservatives and anti-oxidants.

Duration and intensity of cell juice treatments were minimized to eliminate oxidative stresses, hydrolysis, denaturation, isomerization, polymerization and other unwanted processes.

Transformation of the cell juice from the frozen state in 15 liter containers into the initial liquid state was achieved by fluidization over ≤2 minutes. During this treatment cell juice temperature teats increased to only ≤20° C. Short duration of this treatment allowed to minimize both denaturation processes and oxidative damage. Physico-chemical and biochemical properties of the cell juice after its freezing and fluidization were identical to its corresponding properties which were measured during the separation of cell juice from fresh leaves. These properties included but were not limited to its dry matter content, pH, conductivity, red-ox potential, osmolality, and IR spectra.

Then die pH of cell juice which was close to neutral was adjusted using a titration method utilizing 5.0 N Hydrochloric Acid (HCl) to decrease the pH of the cell juice to ≥3.0 (pH adjustment 1). The adjusted cell juice was promptly treated by focused microwave radiation with frequency 2,450 MHz. During this Focused Microwave Processing (FMP) the cell juice temperature was momentarily increased to 90° C. held at this temperature for 1 minute and then the cell juice temperature was immediately decreased to ≤30° C. Then the treated cell juice was quickly separated using continuous flow centrifuge CEPA LE (Carl Padberg Zentrifugenbau GmbH, Germany) at 15,000 rpm and retention time of ≥30 seconds. The separation of 15.0 kg of treated cell juice yielded 1.37 kg of green colored paste precipitate ("Precipitate I") and 13.63 kg of light brown colored slightly opalescent liquid supernatant ("Supernatant I") having dry matter content 6.75%. This Supernatant I was used for further fractionation.

Table 1 represents the data related to the effect of maximum temperature achieved during FMP treatment (Tmax) of pH adjusted cell juice on the dry matter content in Supernatant I, and its color and presence of chlorophyll a and chlorophyll b (determined by the measurements of light absorption at 662 nm and 642 nm respectively).

TABLE 1

Effect FMP Tmax on Selected Parameters of Supernatant I

| FMP Tmax ° C. | Dry Matter % | Color (Gardner Scale) | Absorption at 662 nm | Absorption at 642 nm |
|---|---|---|---|---|
| 20 (control) | 6.19 | 6.5 | 0.044 | 0.032 |
| 60 | 6.45 | 8.0 | 0.017 | 0.014 |
| 90 | 6.95 | 8.5 | <0.005 | <0.005 |
| 120 | 6.39 | 9.0 | <0.005 | <0.005 |
| 140 | 6.35 | 10.5 | <0.005 | <0.005 |
| 150 | 6.33 | 12.5 | <0.005 | <0.005 |
| 170 | 5.72 | 14.5 | <0.005 | <0.005 |
| 200 | 5.44 | 18.5 | <0.005 | <0.005 |

Table 1 data shows that Supernatant I obtained at Tmax=90° C. has higher dry matter content and contains no chlorophyll. Although Gardner Scale value is lower for Supernatant I obtained after Tmax=60° C., this preparation has significantly lower dry matter content and contains higher residual amount of chlorophylls. Beside unwanted presence of this pigment in cosmetic ingredients, chlorophyll can be transformed to pheophorbides which are considered to be toxic compounds (Bergstrom, L. C., Vucenik, I., Hagen, I. K., Chernomorsky S. A., Poretz R. D. In-vitro photocytotoxicity of lysosomotropic immunoliposomes containing pheophorbide a with human bladder carcinoma cells.—J. Photochem. Photobiol., 24, 1, 17-23, 1994) and responsible for skin irritation (Kato T., Yamada K. Relationship between appearance of photosensitization and total pheophorbide level in spirulina powder.—J. Food Hyg. Soc. Japan, 36, 632-634, 1995).

Based on the above reasons, FMP Tmax=90° C. of pH adjusted cell juice was selected as the preferential regime for obtaining Supernatant I which was then used for further fractionation with the objective to improve functional properties including but not limited to color, transparency and stability of personal care ingredient. It should be noted, that Supernatant I had desirable in vitro activities such as (i) enzyme inhibitory activities including but limited to tyrosinase, elastase, trypsin, cyclooxygenase-2 (COX-2) inhibitory activities, (ii) free radical scavenging activity, and (iii) antioxidant activity including but not limited to oxygen radical absorbance capacity. Taking into consideration the critical importance of all above in vitro activities, they should not be impacted by the further treatments required to improve the functional properties of desirable personal care ingredient. With respect to improvement of the composition, Supernatant I should be additionally treated to significantly remove brown pigments and other unwanted compounds including residual proteins.

To achieve this objective Supernatant I was subjected to further treatment including pH adjustments and separations. The first treatment was induced using a titration method utilizing 50% Sodium Hydroxide (NaOH) to increase the pH of cell juice Supernatant I from ~3.0 to ~7.5 (pH adjustment 2). It should be noted, that above pH=7.5, Supernatant H was losing desired elastase and trypsin inhibitory activities. The pH adjustment 2 resulted in darker color of material and developed opalescence which was immediately clarified using continuous flow centrifuge CEPA LE (Carl Padberg Zentrifugenbau GmbH, Germany) at 15000 rpm and retention time of ≥30 sec. The above separation yielded 0.53 kg of brown colored paste precipitate (thereafter Precipitate II) and 13.10 kg of brown colored slightly opalescent supernatant (thereafter Supernatant II) having dry matter content 6.59%.

Supernatant II was then subjected to titration utilizing 5.0 N Hydrochloric Acid (HCl) to decrease the pH value to pH ~3.6 (pH adjustment 3). Such treatment led to lighter color of titrated Supernatant II although its opalescence was slightly increased. This material was treated with sterilizing filtration through membrane having size of pores 0.2 micrometer. This resulted in a light colored transparent Serum Fraction of fresh *ficus* leaves.

The color value of the Serum Fraction (Gardner Scale value=7.0) was lower than color value of Supernatant I (Gardner Scale valve=8.5). It should be noted, that Gardner Scale color value of Serum Fractions was always lower that the color value of corresponding Supernatants I which were obtained at different FMP Tmax conditions (Table 2).

TABLE 2

Effect of FMP Tmax Used for Cell Juice Treatment on the Color (Gardner Scale) of Supernatant I and Serum Fraction.

| FMP Tmax ° C. | Supernatant I | Serum Fraction |
|---|---|---|
| 20 (control) | 6.5 | 6.5 |
| 60 | 8.0 | 7.0 |
| 90 | 8.5 | 7.0 |
| 120 | 9.0 | 7.5 |
| 140 | 10.5 | 7.5 |
| 150 | 12.5 | 10.5 |
| 170 | 14.5 | 13.5 |
| 200 | 18.5 | 15.5 |

Serum Fraction obtained from the cell juice after its fluidization, pH adjustments (within pH range from 3.0 to 7.0), focused microwave radiation (RAP Tmax=90° C. for 1 minute), centrifugal separation and sterilizing filtration demonstrated all desirable enzyme inhibitory activities, free radical scavenging activity, and antioxidant activity.

With respect to determination of residual protein content in Serum Fraction which contains phenolic compounds capable to interfere with colorimetric assays, the Kjeldahl method was used to reliably detect nitrogen content in Serum Fraction and its ultrafiltrates. Different membranes were used to separate Serum Fraction into, three filtrates having molecular weights ≤15, ≤10 and ≤5 kiloDalton (kD) respectively. The data related to nitrogen content in the samples are presented in Table 3.

TABLE 3

Effect of Ultrafiltration Conditions on Nitrogen Content in Filtration Serum Fraction,

| Sample | Nitrogen Content (Kjeldahl Method) % |
|---|---|
| Serum Fraction (control) | 0.064 |
| ≤15 kD Filtrate of Serum Fraction | 0.063 |
| ≤10 kD Filtrate of Serum Fraction | 0.060 |
| ≤5 kD Filtrate of Serum Fraction | 0.059 |

Data shows that nitrogen content was not changed significantly after ultrafiltration even through low molecular weight cut off membrane indicating that practically all nitrogen in Serum Fraction was non-proteinious, i.e. Serum Fraction does not contain proteins.

Further stabilization of Serum Fraction was achieved by adding antioxidants, stabilizers, chelating agents, and preservatives. Below is composition of additives which was utilized to stabilize Serum Fraction as described in present Example 1:0.2% sodium metabisulfite, 0.1% potassium sorbate, 0.1% sodium benzoate, 0.1% sodium methyl paraben. Mixture was incubated until complete solubilization was achieved (≥30 minutes). Then 1.9% pentylene glycol was added to the mixture.

Serum Fraction contained approximately 638 dry matter and its yield from fresh *ficus* leaves was approximately 36%. The yield of Serum Fraction's div matter from 100 kg dry matter of initial fresh *ficus* leaves was approximately 7.2 kg.

Selected characteristics of Serum Fraction and its in vitro activities are presented in Table 4 and Table 5.

TABLE 4

Selected Characteristics of Serum Fraction Obtained from Ficus benghalensis.

| Characteristics | Results |
|---|---|
| Appearance | Clear yellow liquid |
| Odor | Characteristic |
| Solubility in water | Soluble in any ratio |
| Color (Gardner Scale) | 7.0 |
| Dry Matter (%)* | 6.38 |
| Refractive Index (nD) | 1.3479 |
| pH | 4.03 |
| Osmolality (mOsm/kg) | 874 |
| UV spectra features (nm) | Max 200 |
|  | Shoulder ~264 |
|  | Shoulder ~320 |
| Total Plate Count (CFU/10 g) | <10 |
| Mold & Yeast (CFU/10 g) | <10 |
| *Escherichia coli* (CFU/g) | Negative |
| *Salmonella* sp. (CFU/g) | Negative |

TABLE 4-continued

Selected Characteristics of Serum Fraction Obtained from Ficus benghalensis.

| Characteristics | Results |
|---|---|
| *Staphylococcus aureus* (CFU/g) | Negative |
| *Pseudomonas* sp. (CFU/g) | Negative |

*Dry matter (%) is reported for the product before addition of stabilizers.

TABLE 5

Selected In Vitro Activities of Serum Fraction Calculated on Dry Matter ercentage Basis

| Activities | Results |
|---|---|
| Tyrosinase inhibition activity (IC50, mg/ml) | 0.362 |
| Elastase inhibition activity (IC50, mg/ml) | 0.067 |
| Trypsin inhibition activity (IC50, mg/ml) | 0.342 |
| Cyclooxygenase-2 inhibition activity (IC50, mg/ml) | 5.40 |
| Free radical scavenging activity (1/X)* | 2.57 |
| Oxygen radical absorbance capacity (1/Y )** | 0.98 |

*X - number of units dry weight test article to completely scavenge 1 unit dry weight DPPH.
**Y - number of units dry weight test article to produce antioxidant effect equal to effect of 1 unit dry weight (R)-Trolox methyl ether.

Example 2

Comparison of Characteristics and In Vitro Activities of Serum Fractions Obtained from Cell Juice of *Ficus benghalensis*

Fresh *ficus* leaves were collected at different locations and processed into cell juice as described in Example 1. This cell juice was frozen and stored at −30° C. in tightly closed 15 liter rectangular HDPE containers. One or more containers at a time were processed into Serum Fraction using the same procedure as described in Example 1.

Data presented in Table 6 and Table 7 shows variability of selected characteristics and in vitro activities of Serum Fractions obtained from multiple fractionations of the same source of frozen cell juice at different times as well as from fractionations from different frozen cell juice sources.

TABLE 6

Selected Characteristics of Serum Fractions Obtained from Cell Juice of Ficus benghalensis

| Characteristics | Results |
|---|---|
| Appearance | From clear yellow to yellow-reddish liquid |
| Odor | Characteristic |
| Solubility in water | Soluble in any ratio |
| Color (Gardner Scale) | 6.0-7.5 |
| Dry Matter (%)* | 6.08-7.05 |
| Refractive Index (nD) | 1.3479-1.3488 |
| pH | 3.88-4.03 |
| Osmolality (mOsm/kg) | 860-972 |
| UV spectra features (nm) | Max 200 |
|  | Shoulder ~264** |
|  | Shoulder ~280** |
|  | Shoulder ~320** |

*Dry matter (%) is reported for the products before addition of stabilizers.
**Shoulders can be identified in some samples depending on spectra analysis with different setting.

TABLE 7

Selected In Vitro Activities of Serum Fraction
Calculated on Dry Matter Percentage Basis.

| Activities | Results |
| --- | --- |
| Tyrosinase inhibition activity (IC50, mg/ml) | 0.133-0.437 |
| Elastase inhibition activity (IC50, mg/ml) | 0.067-0.103 |
| Trypsin inhibition activity (IC50, mg/ml) | 0.342-1.003 |

Example 3

Preparation of Water Extract of Dried *Ficus benghalensis* Leaves 50 g of air dried *Ficus benghalensis* leaves (collected from the same batch of leaves which was, used in Example 1 were grinded with GM200 Grindomix knife mill (Retsch, Germany) to obtain particles having size <300 micrometer. Grinding included 20 seconds at 2,500 rpm, followed by 10 seconds at 2,500 rpm and then 10 seconds at 10,000 rpm. The minded leaves were homogenized with deionized water using OMNI Programmable Digital Homogenizer (OMNI International, Kennesaw, Ga.). The 35 g of grinded leaves were mixed with 490 a of water and placed in an ice bath on the homogenizer platform. Homogenization was conducted with a 20 mm homogenizer generator for 15 min at 15,000 rpm. The homogenate was then subjected to microwave treatment for 1 minute at 90° C. in an Initiator 2 Focused Microwave Processor (Biotage AB, Uppsala, Sweden). Microwave treated material was then centrifuged for 30 minutes at 3,200 g. The supernatant was then filtered under vacuum through three layers of Whatman No: 2 paper and filtrate was titrated with Hydrochloric Acid (HCl) to pH 4.0. The titrated material was centrifuged for 30 minutes at 3,200 g and the supernatant was then filtered under vacuum through a 0.2 micrometer sterilizing filter. Stabilizers were added to the sample: 0.2% sodium metabisulfite, 0.1% potassium sorbate, 0.1% citric acid, 0.1% sodium benzoate. Mixture was incubated until complete solubilization was achieved 30 minutes). Obtained dried leaf water extract was placed into glass vials and stored in the dark at room temperature. Selected characteristics and in vitro activities of water extract of dried *ficus* leaves are presented in Table 8.1.-(2,3-dihydroxypropyl)pyrrolidin-2-one based lipids are described in WO 2011/056682.

TABLE 8

Selected Characteristics and In Vitro Activities of
Water Extract of Dried *Ficus benghaleusis* Leaves.

| Characteristics or Activities* | Results |
| --- | --- |
| Appearance | Red-brown liquid |
| Odor | Characteristic |
| Solubility in water | Soluble in any ratio |
| Color (Gardner Scale) | 13.0 |
| Dry Matter (%) | 2.23 |
| Refractive Index (nD) | 1.3373 |
| pH | 3.98 |
| Osmolality (mOsm/kg) | 261 |
| UV spectra features (nm) | Max 200 |
| | Shoulder ~278 |
| | Shoulder ~320 |
| Tyrosinase inhibition activity (IC50, mg/ml) | 1.45 |
| Free radical scavenging activity (1/X)** | 3.40 |
| Oxygen radical absorbance capacity (1/Y)*** | 1.04 |

*Presented in vitro activities are calculated on dry matter percentage basis.
**X - number of units dry weight test article to completely scavenge 1 unit dry weight DPPH.
***Y - number of units dry weight test article to produce antioxidant effect equal to effect of 1 unit dry weight (R)-Trolox methyl ether.

Within a broad range of tested concentrations, water extract of dried *ficus* leaves did not demonstrate elastase, trypsin and cyclooxygenase-2 inhibitory activities. Comparison of selected characteristics and in vitro activities of water extract and Serum Fraction obtained from the same batch of *Ficus benghalensis* leaves are presented in Table 9.

TABLE 9

Comparison of Selected Characteristics and In Vitro Activities*
of Water Extract and Serum Fraction Obtained from the Same
Batch of *Ficus benghalensis* leaves.

| Characteristics or Activities | Water Extract | Serum Fraction |
| --- | --- | --- |
| Appearance | Red-brown liquid | Clear yellow liquid |
| Odor | Characteristic | Characteristic |
| Solubility in water | Soluble in any ratio | Soluble in any ratio |
| Color (Gardner Scale) | 13.0 | 7.0 |
| Dry Matter (%) | 2.23 | 6.38 |
| Retractive Index (nD) | 1.3373 | 1.3479 |
| pH | 3.98 | 4.03 |
| Osmolality (mOsm/kg) | 261 | 874 |
| UV spectra features (nm) | Max 200 | Max 200 |
| | Shoulder ~278 | Shoulder ~264 |
| Tyrosinase inhibition activity (IC50, mg/ml) | 0.72 | 0.362 |
| Elastase inhibition activity (IC50, mg/ml) | Not detected | 0.067 |
| Trypsin inhibition activity (IC50, mg/ml) | Not detected | 0.342 |
| Cyclooxygenase-2 inhibition activity (IC50, mg/ml) | Not detected | 5.40 |
| Free radical scavenging activity (1/X)** | 3.40 | 2.57 |
| Oxygen radical absorbance capacity (1/Y)*** | 1.04 | 0.98 |

*Presented in vitro activities are calculated on dry matter percentage basis.
**X - number of units dry weight test article to completely scavenge 1 unit dry weight DPPH.
***Y - number of units dry weight test article to produce antioxidant effect equal to effect of 1 unit dry weight (R)-Trolox methyl ether.

Example 4

Characteristics and In Vitro Activities of Serum Fractions Obtained from Different *Ficus* Species and Locations In addition to *Ficus benghalensis* fresh leaves collected in India and Florida (USA), the fresh leaves of following *ficus* species were used for fractionation to obtain Serum Fraction: *Ficus carica, Ficus elastica, Ficus microcarpa*, and *Ficus trigonata*. Except for *Ficus trigonata*, which was grown in Puerto Rico, these *ficus* species were grown in Florida, USA.

Serum Fractions were obtained via procedure described in Example 1. All of these fractions were compared with respect to their yield, selected physicochemical properties and in vitro activities Table 10, Table 11, and Table 12).

TABLE 10

Comparison of Products of Fractionation of Fresh Ficus Leaves.

| Ficus Species | Fresh Leaves Dry Matter % | Cell Juice Yield % | Cell Juice Dry Matter % | Cell Juice Color | Cell Juice pH | Serum Fraction Yield % | Serum Fraction Dry Matter % |
|---|---|---|---|---|---|---|---|
| F. benghalensis (India) | 32.01 | 51.5 | 9.29 | Light Green | 6.31 | 36.0 | 6.38 |
| F. benghalensis (Florida) | 32.21 | 41.1 | 9.53 | Light Green | 6.08 | 32.2 | 7.05 |
| F. carica (Florida) | 16.25 | 66.1 | 6.38 | Dark Brown | 6.71 | 51.6 | 5.14 |
| F. elastica (Florida) | 19.63 | 60.6 | 6.03 | Brown | 5.60 | 40.6 | 5.43 |
| F. microcarpa (Florida) | 28.76 | 46.2 | 9.13 | Green | 6.74 | 30.1 | 8.06 |
| F. trigonata (Puerto-Rico) | 25.12 | 44.2 | 5.67 | Dark Green | 5.71 | 32.4 | 5.39 |

The above data shows that among different *ficus* species dry matter content, in the fresh leaves, yield of the cell juice and yield of serum fractions as well as their dry matter content, color and pH varied very significantly. The corresponding differences between two *Ficus benghalensis* grown in India and in Florida were less expressed than the differences among different fiats species.

This conclusion is supported by additional data related to the comparison of selected physico-chemical characteristics (Table 11) and in vitro activities of Serum Fractions obtained from different *ficus* species (Table 12).

TABLE 11

Comparison of Serum Fractions Obtained from Different Ficus Species

| | F. benghalensis (India) | F. benghalensis (Florida) | F. carica | F. elastica | F. microcarpa | F. trigonata |
|---|---|---|---|---|---|---|
| Appearance | Clear yellow liquid | Clear yellow liquid | Clear orange liquid | Clear yellow liquid | Clear yellow liquid | Clear orange liquid |
| Odor | Characteristic | Characteristic | Characteristic | Characteristic | Characteristic | Characteristic |
| Solubility in water | Soluble in any ratio | Soluble in any ratio | Soluble in any ratio | Soluble in any ratio | Soluble in any ratio | Soluble in any ratio |
| Color Gardner scale) | 7.0 | 7.5 | 11.5 | 7.5 | 9.5 | 11.5 |
| Dry matter (%) | 6.38 | 7.05 | 5.14 | 5.43 | 8.06 | 5.39 |
| Refractive index (nD) | 1.3479 | 1.3488 | 1.3453 | 1.3456 | 1.3515 | 1.3460 |
| pH | 4.03 | 3.88 | 3.95 | 3.86 | 3.90 | 3.86 |
| Osmolality (mOsm/kg) | 874 | 972 | 801 | 817 | 913 | 817 |
| UV spectra features (nm) | Max 200 Shoulder ~264 Shoulder ~320 | Max 200 Shoulder ~264 Shoulder ~320 | Max 200 Inflection 210 Trough 237 Peak 2.55 Peak 318 | Max 200 Inflection 227 Peak 256 Shoulder ~316 | Max 200 Peak 205 Peak 268 Shoulder ~310 | Max 200 Peak 257 Peak 317 |

TABLE 12

Selected In Vitro Activities* of Ficus serum fractions Obtained from Different Ficus Species.

| | F. benghalensis (India) | F. benghalensis (Florida) | F. carica | F. elastica | F. microcarpa | F. Trigonata |
|---|---|---|---|---|---|---|
| Tyrosinase inhibition activity (IC50, mg/ml) | 0.362 | 0.437 | 0.049 | 0.482 | 0.482 | 0.490 |
| Trypsin inhibition activity (IC50, mg/ml) | 0.342 | 1.003 | 1.074 | >100 (ineffective) | 1.235 | 4.010 |

TABLE 12-continued

Selected In Vitro Activities* of *Ficus* serum fractions Obtained from Different *Ficus* Species.

| | F. benghalensis (India) | F. benghalensis (Florida) | F. carica | F. elastica | F. microcarpa | F. Trigonata |
|---|---|---|---|---|---|---|
| Elastase inhibition activity (IC50, mg/ml) | 0.067 | 0.092 | 1.543 | 1.175 | 0.549 | 1.219 |
| COX-2 inhibition activity (IC50, mg/ml) | 5.40 | 3.1 | >200 (ineffective) | >200 (ineffective) | 0.7 | >200 (ineffective)) |
| Free radical scavenging activity (1/X)** | 2.57 | 2.82 | 11.41 | 11.16 | 3.27 | 4.53 |
| Oxygen radical absorbance capacity (1/Y)*** | 0.98 | 1.01 | 1.88 | 2.91 | 0.54 | 1.18 |

*Presented activities are calculated on dry matter percentage basis.
**X - number of units dry weight test article to completely scavenge 1 unit dry weight DPPH.
***Y - number of units dry weight test article to produce antioxidant effect equal to effect of 1 unit dry weight (R)-Trolox methyl ether.

Example 5

LC/UV/MS Chromatogram Comparisons of Traditional *Ficus* Extract to *Ficus* Serum Fraction (*Ficus benghalensis*)

Components of the *ficus* extract and the FSF were detected by both UV detection from 240-500 Nm and by electrospray mass spectrometry in both positive-ion (m/z 150-1150) and negative-ion (m/z 100-1100) modes after LC separation on a C18 column. Due to high scan rates utilized on a quadrupole MS, only the major components and/or components with high ionization efficiencies were observed in the mass chromatograms. The *ficus* extract from *ficus* serum fraction was analyzed by TOF/MS and structural assignments are based on this exact mass and in-source fragmentation data.

As shown in FIG. 2, the traditional *ficus* extract contains more late-eluting (more hydrophobic) compounds which are not detected in the FSF. As shown in FIG. 3, one group of late-eluting compounds appears to be pheophorbides, which are chlorophyll degradation products. FIG. 4 shows that traditional extract contains higher amounts of what are likely flavonol glycosides. As demonstrated in FIG. 5, the FSF has higher levels, (by about 10×) of catechin and related condensed tannins. However, levels of the three caffeoylquinic acid isomers did not appear to be substantially different between the two samples, as demonstrated in FIG. 6. FIG. 7 demonstrates that FSF contained higher levels of free tyrosine, phenylalanine, and tryptophan.

Method

*Ficus* Serum Fraction Sample Prep

SF was prepared as in Example 1. The FSF sample was diluted 50-fold with 90:10 water:DMSO (20 uL sample+100 uL DMSO+820 uL water) and analyzed by LC/UV/MS according to the conditions below. Approximate solids content in final sample was ~1.26 mg/mL Traditional Sample Prep 10.64 mg of the sample was weighed into a 4 ml glass vial. 1.064 mL of DMSO was added to the vial and sonicated for 30 minutes and occasionally vortexed to mix. 100 uL of this sample was added to a 4 mL glass vial and diluted with 900 uL water. Approximate solids content in final sample ~1 mg/mL HPLC Conditions:
HPLC: Waters Acquity UPLC Binary Solvent Manager S/N M05UPB601M
Waters Acquity UPLC Sample Manager S/N M05UPS632M
Waters Acquity UPLC PDA Detector S/N M05UPD879N
MS: Waters Micromass Quattro Premier MS S/N VAA-219
LC Column: Waters Acquity UPLC BEH C18, 1.7 mm, 2.1×100 mm, part #186002352, lot #0150371861
Mobile Phase A: Water with 0.1% formic acid
B: Acetonitrile with 0.1% formic acid
Separation: Gradient (see Table)

| Time (min) | Flow Rate | % A | % B | Curve |
|---|---|---|---|---|
| Initial | 0.400 mL/min | 95.0 | 5.0 | |
| 0.5 | 0.400 mL/min | 95.0 | 5.0 | 6 |
| 6.5 | 0.400 mL/min | 70 | 30 | 6 |
| 13.5 | 0.400 mL/min | 0.0 | 100.0 | 6 |
| 17.5 | 0.400 mL/min | 0.0 | 100.0 | 6 |
| 18.0 | 0.400 mL/min | 95.0 | 5.0 | 6 |
| 19.0 | 0.400 mL/min | 95.0 | 95.0 | 6 |

Injection Volume: 7.5 uL partial loop; with needle overfill
Column Temperature=25° C.
PDA 240-500 nm at 20 points/sec, filter time constant 0.2 sec, exposure time=automatic, resolution 1.2 nm
MS Conditions:

| | Electrospray (+) | Electrospray (−) |
|---|---|---|
| Capillary (kV) | 3.0 | 3.0 |
| Cone (V) | 30 | 40 |
| Extractor (V) | 2 | 3 |
| RF Lens (V) | 0.2 | 1.0 |
| Source Temperature | 120° C. | 120° C. |
| Desolvation Temperature | 350° C. | 350° C. |
| Cone Gas Flow | 50 L/h | 50 L/h |
| Desolvation Gas Flow | 900 L/h | 800 L/h |
| Scanning Mass Range | 150-1150 | 100-1100 |
| Scan Duration | 0.300 sec | 0.300 sec |
| InterScan Delay | 0.025 sec | 0.025 sec |

Example 6

Melanin Synthesis

A B16-F1 mouse, melanoma cell line is employed in the assay. The B16-F1 cells are obtained from American Tissue Culture Collection, Virginia, USA. The cell culture medium used in the assay comprises 500 mL of Dulbecco's Modified Eagle's Medium (DMEM), 50 mL Fetal Bovine Serum (FBS), and 5 mL of penicillin-streptomycin liquid. B16-F1 cells that are cultured in this medium and grown to greater than 90% confluency synthesize melanin. While not intending to be bound by any theory, it is hypothesized that the melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., California, USA. Equipment used in the assay include a CO2 incubator, such as a Forma. Series Model 3110 by Therma Scientific, Massachusetts, USA a Hemocytometer, such as a Bright Line model by Hauser Scientific, Pennsylvania, USA; and a UV-Visible Spectrum Plate Reader, such as a SpectraMax250 from Molecular Devices, California, USA. The assay steps include:

Day 0—Cell Growth: Warm the cell culture medium to 37° C. and place 29 mL into a T-150 flask. Add approximately 1×106 of B16-F1 passage 1 mouse cells to the T-150 flask and incubate for 3 days at 37° C., 5% CO2, 90% relative humidity, until ~80% confluency;

Day 3—Initiate a 96 Well Plate: At day 3, trypsinize the cells from the T-150 flask and determine the concentration of cells using the Hemacytometer. Initiate a 96 well plate with 2,500 cells per well in 100 uL of cell culture medium. Incubate the plate at 37° C., 5% CO2, 90% relative humidity for 2 days until at least 20% to 40% confluent;

Day 5—Remove the cell culture medium from the plate and replace with fresh culture medium 100 uL per well). Add 1 uL of [test compound] diluted in a [water or DSMO] solvent. Multiple dilution ratios may be tested in order to generate a dose response curve, wherein preferably three wells are treated with each dilution ratio. Controls comprise wells having the cell culture medium, B16-F1 cells, and the solvent (control #1); wells comprising the cell culture medium and the solvent (control #2); and optionally wells comprising the cell culture medium, solvent and [test compound] when necessary to control for the [test compound] background color (control #3);

Day 7—Measure Melanin Production: Cells should have a confluency greater than ~90%. If not, this data point is not used. Add 100 uL of a 0.75% sodium hydroxide solution to each well. Read the 96 well plate using the UV-Vis Plate Reader at 410 nm to optically measure the amount of melanin produced between wells that are treated with [test compound] and control wells that are not. Wells in which melanin is produced appear brownish in color. Wells in which little melanin is produced appear clear to light purple in color. Percentage of melanin synthesis inhibition is calculated by the following equation:

$$100-[\text{OD410 Test Compound}-\text{OD410 Control \#2}] \times 100$$

(OD410 control #1−OD410 Control #2)

Where OD410 is the Optical Density at 410 nm as measured by the UV-Vis Spectrum Plate Reader.

When Control #3 is used, the formula for percentage melanin synthesis inhibition is:

$$100-[\text{OD410 Test Compound}-\text{OD410 Control \#3}] \times 100$$

(OD410 control #1−OD410 Control #2) Control™2)

Using generally the assay outlined above, melanin synthesis in FSF treated B16-F1 cells was inhibited as compared to control cells as shown below in Table 13.

TABLE 13a

FSF B16 data

| | FSF Concentration (w/v %) | | | | | |
|---|---|---|---|---|---|---|
| | 1% | 0.2% | 0.04% | 0.008% | 0.0016% | 0.000064% |
| Percent inhibition | 48.1% | 11.4% | 5.5% | 5.5% | −3% | −1.6% |
| Confluency (visual inspection) | >90% | >90% | >90% | >90% | >90% | >90% |

TABLE 13b

Ficus Dry Leaf Solvent Extract

| Dry Leaf Solvent Extract dilution | % Inhibition Ficus R |
|---|---|
| 0.01 | 23 |
| 0.005 | 8 |
| 0.0025 | 1 |
| 0.00125 | −8 |
| 0.000625 | −3 |
| 0.0003125 | −2 |
| 0.00015625 | 2 |
| 0.000078125 | 2 |

While not necessarily predicative of an in vivo outcome with respect to facial hyper pigmented spots in humans in view of variables such as the complexities of melanin production and transfer within skin and the skin penetration capability of a test compound, this assay does demonstrate an ability for materials, such as FSF, to potentially impact tyrosinase activity.

Example 7

Tyrosinase Inhibition

Tyrosinase is an important enzyme in the biosynthesis of melanin. This assay can identify agents that can interfere with the ability of mushroom tyrosinase enzyme to convert L-tyrosine to L-dihydroxyphenylalanine (L-DOPA).

Reagents and Supplies

Tyrosinase Enzyme: Mushroom Tyrosinase, available from Sigma-Aldrich, Missouri, USA;

Enzyme Substrate: L-tyronsine, available from Sigma-Aldrich, Missouri, USA; Buffer: Phosphate Buffered Saline (PBS), available from Invitrogen, California, USA;
Positive Control: 4-Hydroxyphenyl-β-D-glucopyranoside (Arbutin) available from Sigma-Aldrich, Missouri, USA;
Dimethyl sulfoxide (DSMO), available from Sigma-Aldrich, Missouri, USA;
Falcon 1172 Microtest™ non-tissue culture treated, clear, flat bottom 96 well plates; USA;
Potential Tyrosinase Inhibitor;
Well Plate Reader: Spectra MAX Plus, available from Molecular Devices, California, USA;
Data Acquisition and Analysis Software: SoftMax Pro, available from Molecular Devices, California, USA

| Concentration in Assay | Working Solution Concentration: | Final |
|---|---|---|
| Tyrosinase Enzyme: | 26 Units/mL | 13 Units/mL |
| L-tyrosine Substrate: | 1 mM | 0.5 mM |
| Arbutin positive control: | 20 mM | 200 uM |

Assay Protocol:

Prepare Reagents and Positive Controls

Enzyme substrate working solution of 1 mM is prepared by adding 0.01812 g L-20 tyrosine to 100 mL 1×PBS. Sonicate until L-tyrosine is dissolved. Vortex as necessary. Store at 4° C. when not in use Prepare a 0.2M stock solution of Arbutin positive control by adding 0.0544 g Arbutin to 1 mL DMSO. Vortex and sonicate for 1 minute until Arbutin is dissolved. Dilute this solution 1:10 by adding 100 uL to 900 μL DMSO for a working solution of 20 mM Arbutin. Store at room temperature until used.

Potential tyrosinase inhibitors should be prepared in DMSO. Final volume of test compound in the assay is 21, so working solutions are typically made up at 5-40 mM (100×) which yields a final concentration of 50-400 M in the assay.

Reconstitute tyrosinase enzyme at 1000 U/mL with cold 1×PBS. Store this stock solution in 1 mL aliquots protected from light at −20° C. until needed. Enzyme working solution of 26 U/mL, is prepared by adding 1 ml thawed stock solution (1000 U/ml) to 37.5 cold 1×PBS buffer. This is enough to run four 96-well plates. Protect from tight and keep on ice until used in the assay.

Run Assay

Add 200 uL 1×PBS buffer to triplicate wells on each test plate for proper blank.
Add 2 uL DMSO to triplicate wells for a vehicle control.
Add 2 uL Arbutin to triplicate wells for a positive control.
Add 2 uL of the potential tyrosinase inhibitor to triplicate wells.
Add 98 uL tyrosinase enzyme working solution to each well except blanks. Mix the compounds with the enzyme by pipetting up & down twice or vortex briefly.
Add 100 uL/well of L-tyrosine substrate.
Choose kinetic setting on the SpectraMax 250 Plate Reader and record absorbance readings at 475 nm every 1 minute for 1 hour.
Calculate the slope for the controls and test compounds using the Data Acquisition Software.

The percentage of tyrosinase inhibition is calculated by the following formula:

$$((\text{Avg. vehicle control slope} - \text{Avg. sample slope}) \times 100)/\text{Avg. vehicle control slope}$$

Using generally the assay outlined above, FSF inhibited tyrosinase activity as shown in Table 14 below.

TABLE 14

| Concentration (w/v %) | Tyrosinase Inhibition |
|---|---|
| 1% | 60% |
| 0.5% | 64% |
| 0.25% | 73% |
| 0.125% | 77% |

While not necessarily predicative of an in vivo outcome with respect to facial hyperpigmented spots in humans in view of variables such as the complexities of melanin production and transfer within skin and the skin penetration capability of a test compound, this assay does demonstrate an ability for materials, such, as FSF, to potentially impact tyrosinase activity.

Example 8

In Vivo Testing for Hyperpigmented Spot Reduction and Melanin Evenness

A 9 week in-vivo study was conducted using a round robin, vehicle controlled, split face design including a 1 week normalization period with 270 subjects. The 270 subjects were screened according to inclusion/exclusion criteria which included the following:

Inclusion

Has hyperpigmented spots around cheek and/or periorbital area on both sides of the face.
Has at least 1 hyperpigmented spot of 8-10 mm diameter, 4 spots of 4-6 mm or 10 spots of 2-3 mm diameter (sun spots., freckles, or melasma spots) or
equivalent spot area in the cheek area on each side of their face.
Is willing to refrain from sun exposure by using supplied UV lotion and physical UV blocks, such as a hat, to avoid facial sunburn, tanning or wind burn.

Exclusion

Has been diagnosed as having atopy, eczema, psoriasis, or other chronic skin diseases.
Has obvious signs of facial skin disease (e.g., more than 5 pimples, areas of red scaling skin, superficial thin blood vessels, etc.).
Has significant areas of discoloration or scarring on the face.
Has more than 3 prominent moles (<3 mm) on the face.
Two hundred and seventy subjects were recruited for the study. Approximately 60 subjects dropped during the course of the study. Each subject received two coded test formulations for twice daily application to each half of the face. Images of the facial treatment sites were captured at baseline (week 0), and after 4 and 8 weeks of treatment and analyzed for changes to skin color and spot size and color. The product formulations included a vehicle control, the Vehicle+0.55% FSF, and the vehicle+5% vitamin B3 compound (Niacinamide).

Noncontact spectrophotometric intracutaneous analysis (SiaScopy, Astron Clinica, UK) was used to collect and analyze the subject images. The method used a digital camera (e.g., Fuji S2 digital SLR) as a brand spectrometer and a flash lighting source (e.g., Sigma Super flash light source) to recover facial chromophore information. A cross polarized filter was placed in front of the camera and the lighting source to eliminate specular reflection.

Chromophore mapping of the concentration and distribution of eumelanin (melanin) and oxyhaemoglobin produces grayscale concentration maps of each of these chromophores. Image analysis software, such as Optimas 6.5, can be used to select a region of interest in each chromophore map from which mean grayscale values and spot area fraction are calculated. Spot area fraction refers to total area occupied by melanin spots as a percentage of the whole region of interest. A description of one type of chromophore mapping can be found in EP 1,810,614 and "The Distribution of Melanin in Skin Determined In Vivo", British Journal of Dermatology, 2007, pp 620-628.

FSF was the best performer after 4 weeks, significantly ($p<=0.10$) reducing hyperpigmented spots better than the control and 5% vitamin B3 compositions. After 8 weeks, the vitamin B3 composition was the best performer, although the FSF composition was also significantly better than the control at reducing hyperpigmented spots. Table 16 summarizes the image analysis data, wherein SAF is the mean Spot Area Fraction and ΔSAF is the mean change in Spot Area Fraction from baseline (week 0).

TABLE 16

| | Treatment | | | | | | | |
|---|---|---|---|---|---|---|---|---|
| | NC2SAF | | | | Melanin Evenness | | | |
| | Vehicle | | Nia | | Vehicle | | Nia | |
| | 4 weeks | 8 weeks | 4 weeks | 8 weeks | 4 weeks | 8 weeks | 4 weeks | 8 weeks |
| Niacinamide (Nia) | as | sig p = 0.0004 | | | ns | sig p = 0.0027 | | |
| 0.55% FSF | ns | sig p = 0.0402 | ns | ns | ns | dir p = 0.1702 | ns | ns |

Abbreviations used: SAF = spot area fraction; sig = significant ($p < 0.1$); dir = directional ($0.1 < p < 0.2$) trend = ($0.2 < p < 0.3$) ns = not significant ($p > 0.3$).

FSF was significantly better than vehicle for SAF and directionally better than vehicle for melanin evenness Analytical Methods The following analytical methods are used to determine various physical and chemical properties reported in the Examples.

Method for Determination of Dry Matter

Dry Matter level (percentage) was determined by comparing the weight of liquid sample with weight of dried residue after liquid components have evaporated. Disposable aluminum weighing dishes, Ohaus Explorer E00640 balance from Ohaus Corporation (Pine Brook, N.J.) and a Shel Lab model 1400E oven from VWR (West Chester, Pa.) were used in the procedure. Samples were dried for 12 hours in the oven set at 105 C. Weight of tare was subtracted from weight of tare containing liquid sample to receive the "wet" weight. Weight of tare was subtracted from weight of tare containing same sample after drying, to receive "dry" weight. Dry matter level is then equal to "dry" weight divided by "wet" weight, multiplied by 100%.

Method for Determination of Color

Color (Gardner Scale from 0 to 18) was determined using a Lovibond Comparator 3000 (Tintometer Limited of Salisbury, UK) device by comparing the color of test article in transparent glass tribe with colored glass standards set into the two wheels of the device, according to standard procedure for the device as per instruction manual.

Method for Determination of Osmolality

Osmolality was determined by measuring the depression of freezing point of solution compared to freezing point of pure solvent. This measurement was performed on Advanced Model 3250 Single-Sample Osmometer from Advanced Instruments, Inc. (Norwood, Mass.) according to standard procedure for the device as per instruction manual.

Method for Determination of Refractive Index

Refractive index was measured on Arias 500 refractometer from Reichert Analytical Instruments (Depew, N.Y.) with attached external temperature controlled circulator, according to standard procedure for the device as per instruction manual Method for Measurements of UV Spectra Parameters Peaks, troughs and inflections in UV absorbance spectra were determined by Ultrospec 4300 pro UV/Visible spectrophotometer from Biochrom Ltd. (Cambridge, United Kingdom) with fluid-jacketed cell holder and attached external temperature controlled circulator. Quartz cuvettes with 1 cm optical path length were used for the sample diluted with deionized water. Instrument control and data analysis were provided by Wavescan application of SWIFT H software suite from Biochrom Ltd.

Method for Determination of Elastase Inhibitory Activity

Elastase inhibitory activity was determined by a kinetic colorimetric assay adapted for use with 96-well microtiter plates (Corning 3641) from Corning incorporated (Corning, N.Y.) and Synergy 2 microplate reader from BioTek instruments, Inc. (Winooski, Vt.). Enzymatic activity in cleaving the substrate was indicated by a development of yellow color measured as increase in absorbance at 410 nm wavelength. The N-Methoxysuccinyl-Ala-Ala-Pro-Val-pNA substrate (EPC FH237), and elastase (EPC SE563) were obtained from EPC (Elastin Products Company, Inc., Owensville, Mo.). Reaction volume in each well was 200 microliters, with concentration of elastase equal to 0.87 units/ml, and substrate equal to 363 µM. This procedure was adapted from method titled "Assay with N-MeO-Suc-Ala-Ala-Pro-Val-pNA (EPC No. FH237) as substrate" from page 84 of Elastin Products Company, Inc. Research Biochemicals Catalogue (2004, 92 pages).

Method for Determination of Cyclooxygenase-2 Inhibitory Activity

Cyclooxygenase-2 (COX-2) inhibitory activity was determined by Cayman Chemicals COX inhibitor screening ELISA assay kit 560131.

Method for Determination of Antioxidant Activity

Antioxidant activity was determined by ORAC testing using an adaptation of the method described in "Performing Oxygen Radical Absorbance Capacity (ORAC) Assays with Synergy HT Multi-Detection Microplate Reader" Application Note from BioTek available at (www.biotek.com/resources/docs/ORAC_Assay_Application_Note.pdf) for use with Synergy 2 microplate reader front BioTek Instruments, Inc. (Winooski, Vt.). In this assay, AAPH (2,2'-azobis 2-amino-propane) generates reactive oxygen species which damage the fluorescent probe (sodium fluorescein). Antioxidants such as (R)-Trolox methyl ether prevent or slow this damage, and their effects can be quantified by fluorescence measurements. Fluorescence readings were taken with excitation wavelength set at 485 nm and emission wavelength set at 528 nm, with reaction volume of 200 microliters, AAPH concentration of 55 mM, sodium fluorescein concentration of 1.33 µM, and (R)-Trolox methyl ether concentration range between 80 µM and 2 µM. Sodium fluorescein (Fluka 46960), AAPH (Sigma 440914) and (R)-Trolox methyl ether (Fluka 93509) were obtained from Sigma-Aldrich (St. Louis, Mo.). AUC (Area Under Curve) values were calculated as sum of proportions (current fluorescence reading for the well divided by first fluorescence reading for the well). Average of AUC values of wells with deionized water was subtracted from AUC of wells with (R)-Trolox methyl ether and wells with test articles to obtain AUC corresponding, to preservation of fluorescence by antioxidants. A calibration curve was generated as function of a wells' antioxidant-related AUC showing (R)-Trolox methyl ether weight-equivalent ORAC activity. ORAC activity for test articles was then calculated as units weight test article necessary to achieve antioxidant effect equal to one produced by 1 unit weight (R)-Trolox methyl ether.

Method for Determination of Scavenging Activity

Free radical scavenging activity, i.e. DPPH (2,2-Diphenyl-1-Picrylhydrazyl) free radical scavenging activity was determined by a kinetic colorimetric assay adapted for use with glass-coated polypropylene 96-well microtiter plates (catalog number 400 062) from SUN-SRi (Rockwood, Tenn.) and Synergy 2 microplate reader from BioTek Instruments, Inc. (Winooski, Vt.), Absorbance was measured at 515 nm wavelength. Reaction volume in each microplate well was 200 microliters, with initial concentration of MPH equal to 114 µM. L-ascorbic acid was used as positive control. DPPH (Sigma 09132) and USP L-ascorbic acid (Sigma A-2218) were obtained from Sigma-Aldrich (St. Louis, Mo.). Stoichiometry of the reaction was calculated and expressed as units weight test article necessary to quench 1 unit weight DPPH. This method was adapted from procedure described in the article "Use of a free radical method to evaluate antioxidant activity" by W. Brand-Williams et al, published in LWT—Food Science and Technology, Volume 28, Issue 1, 1995, pp 25-30.

Procedure for Rapid Stability Testing Using Temperature Profiling

Provided below is a procedure for rapid stability testing using temperature profiling:
1. Turn on 12 heating blocks and heat at the designated temperatures, and turn on a refrigerator and maintain at the designated temperature, for at least 4 hours before running experiment. In addition to the 12 samples placed in the heating blocks, one sample will be left at room temperature and another will be refrigerated to provide a total of 14 different temperatures. The temperatures are 5, Room Temperature (~23 C), 32, 36, 40, 44, 48, 52, 56, 60, 64, 68, 72 and 75° C. The heating blocks are equipped with aluminum inserts block milled to fit 20 ml vials; these insert blocks fit inside of the heated pocket blocks of the heating blocks. Each heating block should have independent temperature controllers and temperature sensors, and provide control of reaction block temperatures with 0.1 C regulation.
2. Fill with as little headspace as possible 14 vials. The vials can range in size from autosampler vials to scintillation vials, as long as they are all the same size. For purposes of this example, 20 ml vials were used.
3. Prepare a label fix each vial with notebook reference and temperature. It is best to make the labels as small and narrow as possible. Make one extra label without a temperature to display with vials if color is to be evaluated with a color photo.
4. Attach each label to the corresponding vial without obstructing the view of the product in the vial. This is usually done by taping the label to the lid making a long vertical tab which reads from top to bottom. Put the label on the side of lid that is opposite that of any marking on vial so when the photos are taken the labels can be displayed with the best view of the sample in the vial.
5. If evaluating color take an initial photo of the samples with a digital camera. Line the samples up from left to right lowest temperature to highest so that the sample can be clearly seen in vial (turn vial so any labels or printing on the vial does not obstruct the view). Display the extra label so it may be easily read in the image. For consistency make a mark on the lab bench for the position of the vials and the camera so his geometry may be reproduced later. It is recommended that the flash be turned off.
6. Take the pictures in the following ways for these types of sample:
    a. Clear solutions: against a white background use a flash and no desk lamp
    b. Opaque samples: against a black background turn flash off and use desk lamp
7. If doing a chemical analysis sample each vial for an initial reading.

8. Place samples in heating blocks and in the refrigerator recording the date and time.
9. At the chosen time point (by default use 3, 7 and 14 days) remove the samples from the heating blocks and the refrigerator and allow to come to room temperature for at least 30 min.
10. If evaluating color take a new photo using the marks for the vials and camera positions made in step 4. Repeat this at each time point.
11. if doing a chemical analysis then sample each vial at this point. Repeat for each time point.
12. To evaluate color pick a time point, that best discriminates between different products and crop and paste photos together labeling each product. Lines depicting the 6 months and 1 year room temperature equivalent time may be drawn on the image using the stability table. Find the accelerated temperature corresponding to 6 months and 2 year on the table at the given time point and this determines between which vials to draw the line. (See, for example, FIG. 10)
13. For a chemical analysis plot the concentration with respect the temperature for each time point. Draw a smooth line through the data and record the temperature with which the unacceptable threshold is reached. Reference this temperature to the time in the stability table to get the equivalent room temperature. This technique may be applied to the color analysis if the color is measured with a Lab color meter and the color difference is plotted instead of concentration.
14. The stability table assumes an activation energy of 25 kcal/mole. Most hydrolysis and similar reactions are about this energy or higher. If the energy is higher then the product will be more stable and the table will predict the room temperature stability to be less than what it actually is (an over conservative estimate). Sometimes the energy is lower than this. For this reason, if one is doing a chemical analysis it is recommended to take the data generated above and calculate the reactions energies using an Arrhenius plot to confirm that the assumptions are correct.
15. Appendix: Extraction of Lab colors from pictures:
    i. Transfer all photos onto a CD. Measure the average Lab color of each sample using a computer equipped with color measurement software, such as Optimas, and any necessary peripherals.
    ii. Start with the far left 5 C sample and moving from the upper right and dragging down to the lower left select the area of the vial to have the color averaged. Set the 5 C sample as the standard reference (only do this initially with the 5 C sample).
    iii. Record the L, a, b, Std Dev and dEcmc value for each temperature sample. Record the White Point for each picture (should be 255,255,255).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

What is claimed is:

1. A process for making a *Ficus* cell serum fraction composition, said process comprising:
    a. separating *ficus* cell juice from harvested, un-wilted *ficus* leaves to obtain fresh *ficus* cell juice, wherein no exogenous liquid is added prior or during said separating;
    b. filtering said fresh *ficus* cell juice to obtain fiber-free cell juice; and
    c. fractionating said fiber-free cell juice to obtain *Ficus* Serum Fraction, wherein said fractionating comprises:
        (1) removing chlorophyll from said fiber-free cell juice to obtain Supernatant I;
        (2) removing pigments and proteins from Supernatant I to form *Ficus* Serum Fraction, wherein said removing pigments and proteins from Supernatant I comprises:
            i. adjusting the pH of Supernatant I to about 7.5 to form pH-adjusted Supernatant I;
            ii. separating pH-adjusted Supernatant I into Precipitate II and Supernatant II;
            iii. adjusting the pH of Supernatant II to about 3.6 to form pH adjusted Supernatant II;
            iv. separating pH-adjusted Supernatant II into Precipitate III and *Ficus* Serum Fraction; and
        (3) adding stabilizer selected from the group consisting of antioxidants, chelating agents, preservatives and mixtures thereof, to said *Ficus* Serum Fraction.

2. The process of claim 1, wherein said stabilizer is selected from the group consisting of sodium metabisulfite, potassium sorbate, sodium benzoate, sodium methyl paraben, pentylene glycol, and mixtures thereof.

3. The process of claim 2, wherein said composition is stable at room temperature for at least 6 months.

4. The process of claim 3, wherein said composition is stable at room temperature for at least 12 months.

5. The process of claim 4, wherein said composition is stable at room temperature for at least 24 months.

6. The process of claim 1, wherein said *Ficus* leaves are selected from the group of *Ficus* species consisting of *F. benghalensis, F. carica, F. elastica, F. microcarpa, F. trigonata*, and combinations thereof.

7. The process of claim 1, wherein said composition is substantially free of pheophorbides.

8. The process of claim 1, wherein said composition is substantially free of proteins as measured by the Kjeldahl method.

9. The process of claim 1, wherein said composition is water soluble.

10. The process of claim 1, wherein said composition has a Gardner color value of less than 8.

11. The process of claim 1, wherein said composition has a Gardner color value of less than 7.5.

* * * * *